(12) United States Patent
Cho et al.

(10) Patent No.: US 10,718,030 B2
(45) Date of Patent: Jul. 21, 2020

(54) METHODS FOR PREDICTING EFFECTIVENESS OF CHEMOTHERAPY FOR A BREAST CANCER PATIENT

(71) Applicant: GENCURIX INC., Seoul (KR)

(72) Inventors: Sang Rae Cho, Seoul (KR); Young Ho Moon, Seoul (KR); Jin Il Han, Seoul (KR); Young Kee Shin, Seoul (KR)

(73) Assignee: GENCURIX INC., Seoul (KR)

( * ) Notice: Subject to any disclaimer, the term of this patent is extended or adjusted under 35 U.S.C. 154(b) by 0 days.

(21) Appl. No.: 15/938,331

(22) Filed: Mar. 28, 2018

(65) Prior Publication Data

US 2018/0216198 A1 Aug. 2, 2018

Related U.S. Application Data

(63) Continuation-in-part of application No. PCT/KR2017/013404, filed on Nov. 23, 2017.

(30) Foreign Application Priority Data

Nov. 23, 2016 (KR) .................. 10-2016-0156824

(51) Int. Cl.
*C12Q 1/6886* (2018.01)
*C12Q 1/68* (2018.01)
*C12P 19/34* (2006.01)

(52) U.S. Cl.
CPC ............ *C12Q 1/6886* (2013.01); *C12Q 1/68* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

2013/0344482 A1* 12/2013 Shin ................... C12Q 1/6886
435/6.11
2016/0333413 A1 11/2016 Buechler et al.

FOREIGN PATENT DOCUMENTS

KR 10-2012-0079295 7/2012
KR 10-2014-0125239 10/2014
KR 10-2014-0125647 10/2014

OTHER PUBLICATIONS

Chou, Chen-Pin et al. "Ubiquitin-conjugating Enzyme UBE2C is Highly Expressed in Breast Microcalcification Lesions", PLoS One, 2014, vol. 9, No. 4, e93934, inner pp. 1-11.
International Search Report in corresponding PCT Application No. PCT/KR2017/013404, dated Feb. 19, 2018.
Kwon, Mi Jeong, et al. "Identification of Novel Reference Genes Using Multiplatform Expression Data and Their Validation forQuantitive Gene Expression Analysis," PLoS One, Jul. 2009, vol. 4, Issue 7, pp. 1-15.
Bernard, Philip S., et al., "Real-Time PCR Technology for Cancer Diagnostics," Clinical Chemistry (2002), vol. 48:8, pp. 1178-1185.
Goldhirsch, Aron, et al. "Meeting Highlights: International Consensus Panel on the Treatment of Primary Breast Cancer," Journal of Clinical Oncology, Sep. 15, 2001, vol. 19, No. 18, pp. 3817-3827.
Gyungyub Gong, et al., A new molecular prognostic score for predicting the risk of distant metastasis in patients with HR+/HER2− early breast cancer, Scientific Reports | 7:45554 | DOI: 10.1038/srep45554, pp. 1-11, published: Mar. 28, 2017.

* cited by examiner

*Primary Examiner* — Sarae L Bausch
(74) *Attorney, Agent, or Firm* — Leason Ellis LLP

(57) ABSTRACT

The present invention relates to a method of predicting the effectiveness of chemotherapy in a breast cancer patient, and more particularly, to a method for predicting the effectiveness of chemotherapy by measuring the expression levels of genes for predicting prognosis of breast cancer and a standard gene in a biological sample obtained from the breast cancer patient, and a method for predicting the difference between a patient group having a high effectiveness of chemotherapy and a patient group having a low effectiveness of chemotherapy.
Therefore, the method of the present invention can accurately predict the effectiveness of chemotherapy for the breast cancer patient, and can be used for the purpose of presenting clues about the direction of breast cancer treatment in the future.

6 Claims, 8 Drawing Sheets
(5 of 8 Drawing Sheet(s) Filed in Color)
Specification includes a Sequence Listing.

METHODS FOR PREDICTING EFFECTIVENESS OF CHEMOTHERAPY FOR A BREAST CANCER PATIENT

CROSS-REFERENCE TO RELATED APPLICATIONS

The present application is a continuation-in-part of International Application No.: PCT/KR2017/013404, filed on Nov. 23, 2017, which claims priority to Korean Application No.: 10-2016-0156824, filed on Nov. 23, 2016, which are incorporated by reference in their entireties.

INCORPORATION BY REFERENCE OF SEQUENCE LISTING

A sequence listing created on Mar. 27, 2018 as the ASCII text file "10524_006669-US0_ST25" having a file size of 5.34 bytes, is incorporated herein by reference in its entirety.

TECHNICAL FIELD

The present invention relates to a method for predicting effectiveness of chemotherapy for a breast cancer patient, and more particularly to a method for predicting the effectiveness of chemotherapy for a breast cancer patient, the method comprising steps of: (a) measuring mRNA expression level of at least one proliferation-related genes selected from the group consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67), and a BTN3A2 (Butyrophilin subfamily 3 member A2), an immune-related gene from the biological sample obtained from the breast cancer patient; (b) normalizing the mRNA expression level measured in the step (a); and (c) predicting an effectiveness of chemotherapy in the breast cancer patient by a combination of the at least one proliferation-related gene and the immune-related gene normalized in the step (b), wherein the effectiveness of chemotherapy is predicted to be high when the proliferation-related gene is over-expressed and the effectiveness of chemotherapy is predicted to be low when the immune-related gene is over-expressed.

BACKGROUND OF THE INVENTION

Breast cancer is the most common cancer in women and the second most deadly cancer. The prevalence of breast cancer in 2001 was 90-100 per 100,000 people in the United States and 50-70 per 100,000 people in Europe. The onset of this disease is increasing worldwide. Risk factors for breast cancer include race, age, mutations in the cancer suppressor genes BRCA-1, BRCA-2, and p53. Alcohol consumption, high fat diets, lack of exercise, exogenous postmenopausal hormone and ionizing radiation also increase the risk of breast cancer. The prognosis of breast cancer is worse in estrogen receptors and progesterone receptor negative breast cancers (ER- and PR-, respectively), large tumor size, result of a high grade cytologic diagnosis, and people under 35 years of age (Goldhirsch et al. J. Clin. Oncol. 19: 3817-27). Approximately 212,000 new invasive breast cancer cases and 58,000 new noninvasive breast cancer cases were estimated to be diagnosed in 2005 and 40,000 women were expected to die of breast cancer in 2005.

After surgery, current methods of treating breast cancer require additional adjuvant treatment to reduce future recurrence, such chemotherapy, antihormonal therapy, target therapy or radiotherapy. Of these, chemotherapy is one of the anti-cancer therapies. The pathological status of a breast cancer patient varies from patient to patient depending on the condition of the cancer, the size of the tumor, the pathologic stage of the tumor, or other factors. Thus, since different pathological conditions and different responses in a breast cancer patient, some patients may benefit from chemotherapy with anticancer drugs, but others may not. Continuous administration of chemotherapy to patients who are not as effective as chemotherapy may increase the side effects and cause unwanted pain to the patient.

In this regard, prior to the administration of an anti-cancer drug to a breast cancer patient, methods are needed to accurately predict the effectiveness of chemotherapy in those patients.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Technical Problem

Figure 1:
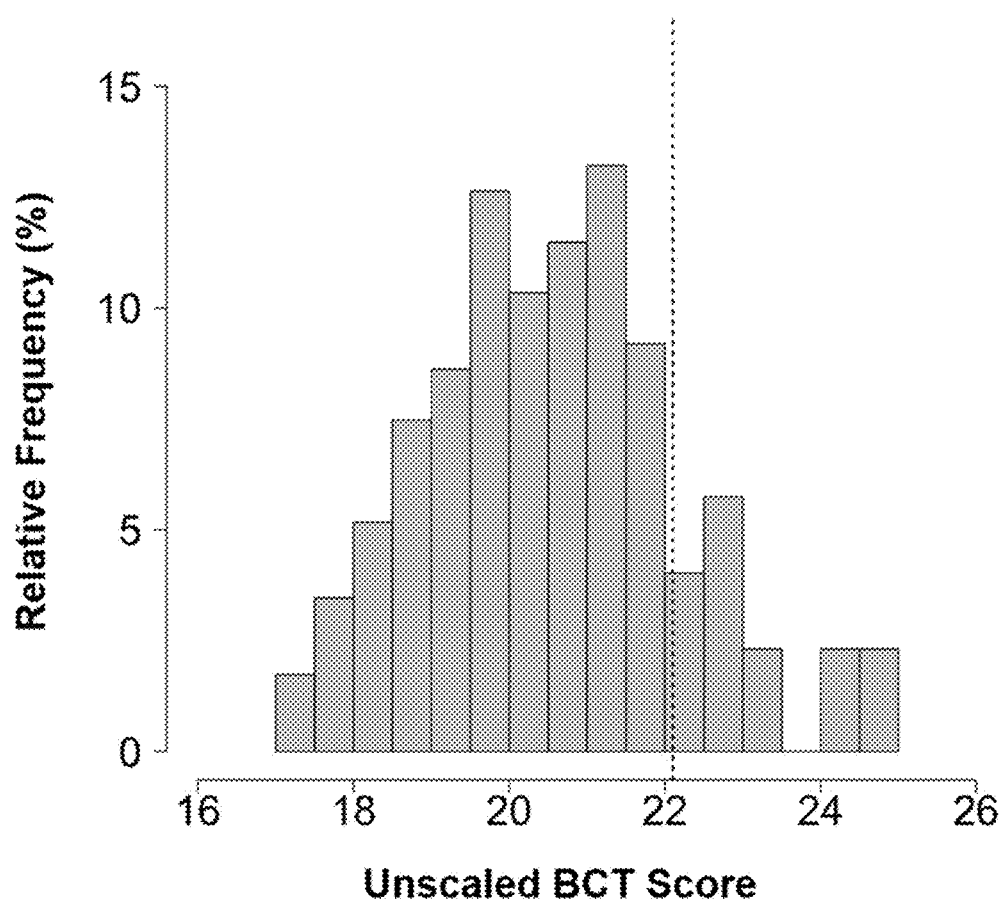
FIG. 1 shows the distribution of unscaled BCT scores in the algorithmic test group.

Accordingly, the present inventors have completed the present invention after they have found that the effectiveness of chemotherapy can be predicted in a breast cancer patient by collecting and analyzing clinical information obtained from breast cancer tissues to identify gene sets related to prognosis prediction, by developing an algorithm that can predict the prognosis of a breast cancer patient by selecting and combining genes and their sets suitable for FFPE samples among the identified genes, and by distinguishing patients according to the above algorithm as a result of the extensive efforts to develop an algorithm for predicting the prognosis of a breast cancer patient using FFPE samples of tissues containing cancer cells of patients and gene information.

Accordingly, an aspect of the present invention is directed to provide a method for predicting the effectiveness of the chemotherapy in a breast cancer patient, the method comprising the steps of:

(a) measuring mRNA expression level of at least one proliferation-related genes selected from the group consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67), and a BTN3A2 (Butyrophilin subfamily 3 member A2), an immune-related gene from the biological sample obtained from the breast cancer patient;

(b) normalizing the mRNA expression level measured in the step (a); and (c) predicting an effectiveness of chemotherapy in the breast cancer patient by a combination of the at least one proliferation-related gene and the immune-related gene normalized in the step (b), wherein the effectiveness of chemotherapy is predicted to be high when the proliferation-related gene is over-expressed and the effectiveness of chemotherapy is predicted to be low when the immune-related gene is over-expressed.

Another aspect of the present invention is to provide a method for predicting the effectiveness of chemotherapy in a breast cancer patient, the method comprising the steps of:

(a) measuring a mRNA expression level of UBE2C (Ubiquitin-conjugating enzyme E2C), TOP2A (Topoisomerase 2 alpha), RRM2 (ribonucleotide reductase M2), FOXM1 (Forkhead box M1) MKI67 (Marker of proliferation Ki-67) and a BTN3A2 (Butyrophilin subfamily 3 member A2) from a biological sample obtained from the breast cancer patient, respectively;

(b) normalizing the mRNA expression level measured in the step (a); and (c) evaluating the size of a tumor and a pN-stage in the breast cancer patient;

(d) calculating a numerical value by putting a normalized value obtained in the step (b), and the size of the tumor and the pN-stage in the step (c) into the following Equations 1 and 2

Unscaled BCT score(U-BS)=$a*\Delta Ct\_UBE2C+ b*\Delta Ct\_TOP2A+c*\Delta Ct\_RRM2+ d*\Delta Ct\_FOXM1+e*\Delta Ct\_MKI67+ f*\Delta Ct\_BTN3A2+g*Tumor\_size(cm)+h*pN(0 \text{ or } 1)$ (Equation 1)

BCT score=0 if 0.8*Unscaled BCT score(U-BS)−13.71<0

BCT score=0.8*U-BS−13.71

BCT score=10 if 0.8*U-BS−13.71>10 (Equation 2)

Wherein the value of the gene used for predicting the effectiveness of chemotherapy is a normalized mRNA expression value calculated using a standard gene; The tumor size is a value determined as the long axis length of the tumor and the pN is a value determined according to the pathological judgment of a lymph node metastasis, Wherein a is 0.16 to 1.09, b is 0 to 0.71, c is 0 to 0.53, d is 0 to 0.57, e is 0 to 0.35, f is −1.02 to 0, g is 0.25 to 1.52 and his 0.19 to 2.25; and (e) predicting that the greater the value calculated in the step (d) is, the greater the effectiveness of chemotherapy is.

Another aspect of the present invention is to provide a composition for predicting the effectiveness of chemotherapy in the breast cancer patient, the composition comprising an agent for measuring the expression level of UBE2C, TOP2A, RRM2, FOXM1, MKI67 and BTN3A2 genes, respectively.

Another aspect of the present invention is to provide a composition for predicting the effectiveness of chemotherapy in the breast cancer patient, the composition consisting of an agent for measuring the expression level of UBE2C, TOP2A, RRM2, FOXM1, MKI67 and BTN3A2 genes, respectively.

Still another aspect of the present invention is to provide a composition for predicting the effectiveness of chemotherapy in the breast cancer patient, the composition essentially consisting of an agent for measuring the expression level of UBE2C, TOP2A, RRM2, FOXM1, MKI67 and BTN3A2 genes, respectively.

Still another aspect of the present invention is to provide a kit for predicting the effectiveness of chemotherapy in the breast cancer patient, the kit comprising an agent for measuring the expression level of UBE2C, TOP2A, RRM2, FOXM1, MKI67 and BTN3A2 genes, respectively.

Still another aspect of the present invention is to provide use of an agent for measuring the expression level of UBE2C, TOP2A, RRM2, FOXM1, MKI67 and BTN3A2 genes for preparing an agent for predicting the effectiveness of chemotherapy of the breast cancer patient.

Technical Solution

An embodiment according to an aspect of the present invention provides a method for predicting the effectiveness of chemotherapy in a breast cancer patient, the method comprising the steps of:

(a) measuring mRNA expression level of at least one proliferation-related genes selected from the group consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67), and a BTN3A2 (Butyrophilin subfamily 3 member A2), an immune-related gene from the biological sample obtained from the breast cancer patient;

(b) normalizing the mRNA expression level measured in the step (a); and (c) predicting an effectiveness of chemotherapy in the breast cancer patient by a combination of the at least one proliferation-related gene and the immune-related gene normalized in the step (b), wherein the effectiveness of chemotherapy is predicted to be high when the proliferation-related gene is over-expressed and the effectiveness of chemotherapy is predicted to be low when the immunological-related gene is over-expressed.

Another embodiment according to an aspect of the present invention provides a method for predicting the effectiveness of chemotherapy in a breast cancer patient, the method comprising the steps of:

(a) measuring a mRNA expression level of UBE2C (Ubiquitin-conjugating enzyme E2C), TOP2A (Topoisomerase 2 alpha), RRM2 (ribonucleotide reductase M2), FOXM1 (Forkhead box M1) MKI67 (Marker of proliferation Ki-67) and a BTN3A2 (Butyrophilin subfamily 3 member A2) from a biological sample obtained from the breast cancer patient, respectively;

(b) normalizing the mRNA expression level measured in the step (a); and (c) evaluating the size of a tumor and a pN-stage in the breast cancer patient;

(d) calculating a numerical value by putting a normalized value obtained in the step (b), and the size of the tumor and the pN-stage in the step (c) into the following Equations 1 and 2

$$\text{Unscaled BCT score(U-BS)} = a*\Delta Ct\_UBE2C + b*\Delta Ct\_TOP2A + c*\Delta Ct\_RRM2 + d*\Delta Ct\_FOXM1 + e*\Delta Ct\_MKI67 + f*\Delta Ct\_BTN3A2 + g*Tumor\_size(cm) + h*pN(0 \text{ or } 1) \quad \text{(Equation 1)}$$

BCT score=0 if 0.8*Unscaled BCT score(U-BS)−13.71<0

BCT score=0.8*U-BS−13.71

BCT score=10 if 0.8*U-BS−13.71>10  (Equation 2)

Wherein the value of the gene used for predicting the effectiveness of chemotherapy is a normalized mRNA expression value calculated using a standard gene; The tumor size is a value determined as the long axis length of the tumor and the pN is a value determined according to the pathological judgment of a lymph node metastasis, Wherein a is 0.16 to 1.09, b is 0 to 0.71, c is 0 to 0.53, d is 0 to 0.57, e is 0 to 0.35, f is −1.02 to 0, g is 0.25 to 1.52 and h is 0.19 to 2.25; and (e) predicting that the greater the value calculated in the step (d) is, the greater the effectiveness of chemotherapy is.

Another embodiment according to an aspect of the present invention provides a composition for predicting the effectiveness of chemotherapy in the breast cancer patient, the composition comprising an agent for measuring the expression level of UBE2C, TOP2A, RRM2, FOXM1, MKI67 and BTN3A2 genes, respectively.

An embodiment according to another aspect of the present invention provides a composition for predicting the effectiveness of chemotherapy in the breast cancer patient, the composition consisting of an agent for measuring the expression level of UBE2C, TOP2A, RRM2, FOXM1, MKI67 and BTN3A2 genes, respectively.

An embodiment according to still another aspect of the present invention provides a composition for predicting the effectiveness of chemotherapy in the breast cancer patient, the composition essentially consisting of an agent for measuring the expression level of UBE2C, TOP2A, RRM2, FOXM1, MKI67 and BTN3A2 genes, respectively.

An embodiment according to another aspect of the present invention provides a kit for predicting the effectiveness of chemotherapy in the breast cancer patient, the kit comprising an agent for measuring the expression level of UBE2C, TOP2A, RRM2, FOXM1, MKI67 and BTN3A2 genes, respectively.

An embodiment according to another aspect of the present invention provides a use of an agent for measuring the expression levels of UBE2C, TOP2A, RRM2, FOXM1, MKI67 and BTN3A2 genes for preparing an agent for predicting the effectiveness of chemotherapy of the breast cancer patient.

Hereinafter, the present invention will be described in detail.

The present invention provides a method for predicting the effectiveness of chemotherapy in a breast cancer patient, the method comprising the steps of:

(a) measuring mRNA expression level of at least one proliferation-related genes selected from the group consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67), and a BTN3A2 (Butyrophilin subfamily 3 member A2), an immune-related gene from the biological sample obtained from the breast cancer patient;

(b) normalizing the mRNA expression level measured in the step (a); and (c) predicting an effectiveness of chemotherapy in the breast cancer patient by a combination of the at least one proliferation-related gene and the immune-related gene normalized in the step (b), wherein the effectiveness of chemotherapy is predicted to be high when the proliferation-related gene is over-expressed and the effectiveness of chemotherapy is predicted to be low when the immune-related gene is over-expressed.

The term "the effectiveness of the chemotherapy" in the present invention means whether an effective therapeutic effect will be exhibited when a therapeutic treatment of administering an anti-cancer drug such as a chemical substance to the breast cancer patient is carried out. The above-mentioned "effective therapeutic effect" is a concept comprising full recovery of cancer, recurrence, metastasis or metastatic recurrence, and most preferably refers to metastatic recurrence, but is not limited thereto.

The "metastatic recurrence" in the present invention is a concept comprising local metastatic recurrence that occurs in breast cancer site before treatment and/or the ipsilateral breast and/or the contralateral breast, and the distant metastatic recurrence that occurs in distant areas such as the lung, liver, bone, lymph nodes, skin, and brain. Preferably, in the present invention, the metastatic recurrence may be distant metastatic recurrence, but is not limited to.

The term "metastasis" in the present invention means, after the initial treatment, that cancer cells derived and modified from at least one breast tumor continue to grow to be cancer at the site remote from the tumor (hereinafter referred to as "distant area"). The distant area may be, for example, in one or more lymph nodes, which may be mobile or fixed, ipsilateral or contralateral to the tumor, and the collarbone or underarm.

The predictability of the effectiveness of chemotherapy of the breast cancer patient is mainly determined by the stage of disease after surgery to evaluate the size of the tumor (T), the metastasis to the periphery of the lymph nodes (N), and the distant metastasis (M) (TNM staging). The predictability of the effectiveness of chemotherapy in patients classified according to TNM stage is also different even in the same stage. Thus, the effectiveness of chemotherapy in breast cancer of the same stage can be determined by expression of estrogen or progesterone receptor (ER or PR) and overexpression of HER2 (human epidermal growth factor receptor 2) or amplification of the gene. Even breast cancer of the same stage, the pathology and prognosis vary significantly depending on the expression of estrogen receptor, progesterone receptor or HER2, so it is necessary to clearly distinguish it and to set the treatment method specifically.

Therefore, recently, the characteristics of breast cancer were classified by gene and molecular biology (Table 1).

According to the subtype, the outcome and prognosis of treatment are different, and it is used as an index for selection of surgical method or chemotherapy.

TABLE 1

Molecular biological subtype classification of breast cancer

| Subtype | Characterization | Frequency (%) |
|---|---|---|
| Luminal A type | ER positive and/or PR positive HER2 negative Low expression of Ki67 | 30~70 |
| Luminal B type | ER positive and/or PR positive HER2 positive (or high expression of Ki67 and HER2 negative) | 10~20 |
| Triple negative type | ER negative PR negative HER2 negative | 15~20 |
| HER2 type | ER negative PR negative HER2 positive | 5~15 |

The breast cancer in the present invention is preferably an estrogen receptor and/or progesterone receptor-positive and HER2 negative breast cancer, and most preferably it can be a Luminal A type breast cancer, but is not limited thereto.

In the case of breast cancer, the higher the stage is, the more advanced the cancer is, and the prognosis is also not good. Breast cancer is divided into 0 to 4 stages. Breast cancer uses TNM staging system, and three factors are required to determine TNM staging. There is a T stage determined by the size and character of the cancer itself, an N stage determined by the degree of involvement of the lymph nodes, and an M stage determined by whether there is metastasis to other sites other than the breast. The pathological characteristics in each stage are summarized in Table 2 below.

TABLE 2

Pathologic classification of breast cancer according to TNM stage

| Classification | Detailed divisions |
|---|---|
| T stage | T0: No evidence of tumor Tis: Intraepithelial cancer T1: The maximum diameter of the chest is less than 2 cm T2: The maximum diameter of the dose is greater than 2 cm but less than 5 cm T3: The maximal straightness of the dose is greater than 5 cm |
| N stage | N0: No lymph node metastasis N1: Number of metastatic lymph nodes is 1 to 3 N2: The number of metastatic lymph nodes is more than 4 but less than 9 N3: The number of lymph nodes is more than 10 |
| M stage | M0: No remote transition M1: There is a remote transition |

In the present invention, the breast cancer is preferably an early stage breast cancer, more preferably a breast cancer corresponding to pN0 or pN1 stage, most preferably a breast cancer classified as 1 or 2 stage according to the TNM stage, but it is not limited to.

Hereinafter, each step of the method for predicting the effectiveness of chemotherapy for the breast cancer patient is described in detail.

(a) obtaining a biological sample from the breast cancer patient;

In the present invention, the biological sample may be a breast cancer tissue of the breast cancer patient. The breast cancer tissue may also contain some normal cells, preferably a formalin-fixed paraffin-embedded (FFPE) tissue, a fresh tissue, and a frozen tissue containing cancer cells of a patient, but is not limited thereto.

(b) measuring mRNA expression level of at least one proliferation-related genes selected from the group consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67), and a BTN3A2 (Butyrophilin subfamily 3 member A2) immune-related gene from the sample in the (a).

A predictive marker of the effectiveness of chemotherapy in the breast cancer patient in the present invention can be proliferation-related genes consisting of UBE2C (Ubiquitin-conjugating enzyme E2C), TOP2A (Topoisomerase 2 alpha), RRM2 (ribonucleotide reductase M2), FOXM1 (Forkhead box M1) and MKI67 (Marker of proliferation Ki-67) and a BTN3A2 (Butyrophilin subfamily 3 member A2), an immune-related gene. Each of these may be independently selected, but may be used to predict the effectiveness of chemotherapy in the breast cancer patient, preferably by a combination of two or more genes.

Each of the above genes may be a sequence of each gene or a synonym of each gene known in the art, preferably a sequence of each gene derived from a human, more preferably UBE2C (Gene ID: 11065), TOP2A (Gene ID: 7153), RRM2 (Gene ID: 6241), FOXM1 (Gene ID: 2305), MKI67 (Gene ID: 4288), BTN3A2 (Gene ID: 11118), but is not limited thereto.

Synonyms and sequences for each gene can be found in GenBank.

In the present invention, the mRNA expression level can be measured by any method performed in the art to measure the expression level of the gene. Preferably, the methods can be performed using a microarray, a polymerase chain reaction (PCR), RT-PCR (qRT-PCR), real-time PCR, northern blot, DNA chip and RNA chip, but are not limited thereto.

The measurement of the expression level of the gene of interest of the present invention is preferably a detection of the expression level of the gene of interest, more preferably the quantitative detection of the expression level of the gene of interest. In order to detect the expression level, mRNA isolation in the sample tissue and cDNA synthesis in the mRNA may be necessary. In order to isolate mRNA, a method of isolating RNA in a sample known in the art can be used. Preferably, the sample is an FFPE sample, and thus it may be a method of separating mRNA suitable for FFPE sample. As the cDNA synthesis process, a cDNA synthesis method known in the art using mRNA as a template can be used. Preferably, the expression level of the predictive marker of the effectiveness of chemotherapy in the the breast cancer patient of the present invention is quantitative detection of mRNA expression in the FFPE sample. Therefore, it can be measured by the mRNA isolation method for FFPE samples and real time reverse transcription quantitative polymerase chain reaction (RT-qPCR).

In addition, measurement of the expression level of the gene of interest in the present invention can be performed according to a method known in the art, but can be measured by an optical quantitative analysis system using a probe labeled with a reporter fluorescent dye and/or a quencher fluorescent dye. The measurement may be performed by a commercially available equipment, for example, a system such as ABIPRISM 7700™ Sequence Detection System™, Roche Molecular Biochemicals Lightcycler, and software attached thereto. Such measurement data can be expressed as a measurement value or a threshold cycle (Ct or Cp). The point at which the measured fluorescence value is recorded as the first statistically significant point is the threshold cycle. This indicates that the detection target appears in inverse proportion to the initial value existing as a template of the PCR reaction, so that when the value of the threshold cycle is smaller, targets to detect exist more quantitatively.

(c) normalizing the mRNA expression level measured in the (b);

The expression levels of the genes to be detected in the present invention may be different in expression amounts of overall genes or expression levels depending on the patient or the sample, so the normalization is required. The normalization is accomplished through differences in expression amounts or expression levels of genes that may indicate differences in basal expression amounts or expression levels. Preferably, it calculates a ratio of an average expression amount of one to three genes (or the average of these expression amounts when a plurality of genes are selected) in CTBP1 (C-terminal-binding protein 1), CUL1 (cullin 1) and UBQLN1 (Ubiquilin-1).

(d) predicting an effectiveness of chemotherapy in the breast cancer patient by a combination of the at least one proliferation-related gene and the immune-related gene normalized in the step (b), wherein the effectiveness of chemotherapy is predicted to be high when the proliferation-related gene is over-expressed and the effectiveness of chemotherapy is predicted to be low when the immunel-related gene is over-expressed.

In the present invention, the term 'high effectiveness of chemotherapy' means that the probability of metastasis, recurrence or metastatic recurrence of cancer after chemotherapy is lower than when chemotherapy is not given. In other words, it can be said that it is preferable to carry out the chemotherapy because it is more effective than the side effect of chemotherapy.

Meanwhile, the above 'low effectiveness of chemotherapy' means that the probability of metastasis, recurrent or metastatic recurrence after receiving chemotherapy is not significantly changed or even a worse prognosis compared to when chemotherapy is not given. In other words, it can be said that it is preferable to not perform the chemotherapy because the effect of chemotherapy cannot be expected and side effects are present.

Preferably, the 'high effectiveness of chemotherapy' means that the probability of metastasis, recurrence or metastatic recurrence of cancer is lower within 10 years than when chemotherapy is not given, and the 'low effectiveness of chemotherapy' means that the probability of metastasis, recurrence or metastatic recurrence is not changed, or even more increased within 10 years compared to when chemotherapy is not given.

The term '10 years' refers to 10 years from the time point when the cancer is removed by surgery of patients with the primary breast cancer (i.e., the starting point of surgery).

In the present invention, the overexpression of the proliferation-related genes is closely related to the bad prognosis in the breast cancer patient and the high effectiveness of chemotherapy. The overexpression of the above-mentioned immune-related gene is closely related to the good prognosis in the breast cancer patient and the low effectiveness of chemotherapy. Therefore, the effectiveness of chemotherapy can be more accurately predicted by combining the expression pattern of the proliferation-related genes and the immune-related gene.

That is, the gene combination of the present invention can be used to select patients who do not need additional chemotherapy after surgery for primary breast cancer. The target patient group of the gene combination in the present invention is preferably a group of patients who have not undergone any chemotherapy even before and after the surgery, and it is said to be a patient group who wants to decide whether receiving chemotherapy will be beneficial or not receiving chemotherapy will be beneficial for the progress of the disease in the future.

In the present invention, patients with the low effectiveness of chemotherapy are those who are predicted not to have a poor prognosis of the breast cancer patient (i.e., who are expected to have a "good prognosis" in the future) and do not require additional chemotherapy after surgery because of the low probability of metastasis, recurrence or metastatic recurrence within 10 years. However, patients with the high effectiveness of chemotherapy are those who are predicted to have a poor prognosis of the breast cancer patient (i.e., who are expected to have a "bad prognosis" in the future), and require additional chemotherapy after surgery because of the high probability of metastasis, recurrence or metastatic recurrence within 10 years. In other words, patients who are predicted not to have a bad prognosis of breast cancer can be determined to be more advantageous for the progression of breast cancer without chemotherapy in the future because the side effects due to the chemotherapy are larger than the therapeutic effect. However, patients who are predicted to have a poor prognosis of the breast cancer patient can be determined to be more advantageous for the progression of breast cancer with the chemotherapy in the future because the therapeutic effect are larger than the side effects due to the chemotherapy.

In addition, the present invention further includes a step of evaluating the size and pN-stage of the tumor after the (b). In the (d), The present invention provides a method for predicting the effectiveness of chemotherapy in the breast cancer patient, which is characterized that if the size of the tumor is larger and the pN stage is higher, it is determined that the effectiveness of chemotherapy is high.

In other words, the effectiveness of chemotherapy can be more accurately predicted by combining the expression of the proliferation-related genes, the expression of the immune-related genes, the size of the tumor and the pN-stage, and the method for predicting the effectiveness of chemotherapy in the breast cancer patient through such a combination have not been reported in the past.

In the present invention, the size of the tumor refers to the length of the major axis of the cancer, preferably the length of the major axis of the cancer measured by a pathologist. The size of the tumor is expressed in centimeters.

In the present invention, the pN refers to a method of determining the metastasis to the lymph node by a pathological classification among the methods of classifying the stage of breast cancer. The method of the pathological classification is also called postsurgical histopathological classification. It is a method of distinguishing pathologic stages by collecting information from surgical or pathological examinations together with the information obtained before starting treatment in the breast cancer patient.

The pN is a method of discrimination based on the degree of metastasis to the lymph nodes. The axillary lymph nodes are resected to determine whether the tumor is metastasized. The higher the pN level is, the more metastasis of tumor cell to the lymph nodes has occurred. So the effectiveness of chemotherapy can be determined to be high because the prognosis of breast cancer was poor.

In the present invention, the pN may preferably be the pN0 or the pN1, but is not limited thereto. The pN0 refers to a stage where metastasis to the local lymph node is not observed. The pN1 refers a stage in which micrometastases in one to three ipsilateral axillary lymph nodes are found.

Therefore, by determining the size of the tumor and the pN stage as a prognostic predictor or a predictor of the effectiveness of chemotherapy of the the breast cancer patient together with the expression levels of the genes measured in the (b) according to the above method, the prognosis of the breast cancer patient and the effectiveness of chemotherapy can be more accurately predicted.

The present invention provides a method for predicting the effectiveness of chemotherapy of the breast cancer patient, the method comprising the steps of:

(a) obtaining a biological sample from the breast cancer patient;

(b) measuring a mRNA expression level of UBE2C (Ubiquitin-conjugating enzyme E2C), TOP2A (Topoisomerase 2 alpha), RRM2 (ribonucleotide reductase M2), FOXM1 (Forkhead box M1) MKI67 (Marker of proliferation Ki-67) and a BTN3A2 (Butyrophilin subfamily 3 member A2) from a biological sample obtained from the breast cancer patient, respectively;

(c) normalizing the mRNA expression level measured in the step (b); and (d) evaluating the size of a tumor and a pN-stage in the breast cancer patient;

(e) calculating a numerical value by putting a normalized value obtained in the step (c), and the size of the tumor and the pN-stage in the step (d) into the following Equations 1 and 2

Unscaled BCT score(U-BS)=$a*\Delta Ct\_UBE2C+ b*\Delta Ct\_TOP2A+c*\Delta Ct\_RRM2+ d*\Delta Ct\_FOXM1+e*\Delta Ct\_MKI67+ f*\Delta Ct\_BTN3A2+g*Tumor\_size(cm)+h*pN$(0 or 1)        (Equation 1)

BCT score=0 if 0.8*Unscaled BCT score(U-BS)−13.71<0

BCT score=0.8*U-BS−13.71

BCT score=10 if 0.8*U-BS−13.71>10        (Equation 2)

Wherein the value of the gene used for predicting the effectiveness of chemotherapy is a normalized mRNA expression value calculated using a standard gene; The tumor size is a value determined as the long axis length of the tumor and the pN is a value determined according to the pathological judgment of a lymph node metastasis, Wherein a is 0.16 to 1.09, b is 0 to 0.71, c is 0 to 0.53, d is 0 to 0.57, e is 0 to 0.35, f is −1.02 to 0, g is 0.25 to 1.52 and his 0.19 to 2.25; and (f) predicting that the greater the value calculated in the step (e) is, the greater the effectiveness of chemotherapy is. The (a) to (d) are the same as described above.

(e) calculating a numerical value by putting a normalized value obtained in the step (c), and the size of the tumor and the pN-stage in the step (d) into the following Equations 1 and 2

Unscaled BCT score(U-BS)=$a*\Delta Ct\_UBE2C+ b*\Delta Ct\_TOP2A+c*\Delta Ct\_RRM2+ d*\Delta Ct\_FOXM1+e*\Delta Ct\_MKI67+ f*\Delta Ct\_BTN3A2+g*Tumor\_size(cm)+h*pN$(0 or 1)        (Equation 1)

BCT score=0 if 0.8*Unscaled BCT score(U-BS)−13.71<0

BCT score=0.8*U-BS−13.71

BCT score=10 if 0.8*U-BS−13.71>10        (Equation 2)

Wherein the value of the gene used for predicting the effectiveness of chemotherapy is a normalized mRNA expression value calculated using a standard gene; The tumor size is a value determined as the long axis length of the tumor and the pN is a value determined according to the pathological judgment of a lymph node metastasis, Wherein a is 0.16 to 1.09, b is 0 to 0.71, c is 0 to 0.53, d is 0 to 0.57, e is 0 to 0.35, f is −1.02 to 0, g is 0.25 to 1.52 and h is 0.19 to 2.25;

The score of predicting prognosis is calculated by linear combination of the gene and the coefficient corresponding to each tumor size and pN. The proliferation gene, tumor size, and pN have a positive coefficient, and the immune gene has a negative coefficient. Each coefficient is applied within a 95% confidence interval of the calculated coefficient value (point estimate) as a result of the survival analysis, and preferably the point estimate of each coefficient is used.

| Coefficient | Point estimate | 95% confidence interval |
|---|---|---|
| a (UBE2C) | 0.63 | 0.16~1.09 |
| b (TOP2A) | 0.32 | 0.00~0.71 |
| c (RRM2) | 0.13 | 0.00~0.53 |
| d (FOXM1) | 0.02 | 0.00~0.57 |
| e (MKI67) | 0.04 | 0.00~0.35 |
| f (BTN3A2) | −0.42 | −1.02~0.00 |
| g (Tumor size) | 0.89 | 0.25~1.52 |
| h (pN) | 1.22 | 0.19~2.25 |

Preferably, the method for predicting the effectiveness of chemotherapy of the breast cancer patient according to the present invention is related to the two major biological characteristics that govern the clinical outcome of the breast cancer patient, namely immune response and cell proliferation. Genes which were expressed stably in FFPE tissue specimens and shown large different expression according to prognosis were screened. The coefficients for the genes and two important clinical information (the tumor size and the pN stage) for prognosis were calculated by Cox analysis and the BCT score can be obtained by multiplying expression values of normalized genes, the tumor size and the pN stage according to the following Equation 1 to predict the effectiveness of chemotherapy.

Unscaled BCT score=$0.63*\Delta Ct\_UBE2C+ 0.32*\Delta Ct\_TOP2A+0.13*\Delta Ct\_RRM2+ 0.02*\Delta Ct\_FOXM1+0.04*\Delta Ct\_MKI67− 0.42*\Delta Ct\_BTN3A2+0.89*Tumor\_size(cm)+ 1.22*pN$(0 or 1)        (Equation 1)

The degree to which the prognostic factors (genes, clinical information) affect the survival rate can be shown as a quantitative value by Cox proportional hazards analysis. The Cox proportional hazards model expresses the degree of the prognostic factors affecting the survival rate through the relative hazard ratio (HR), which is a proportion of the risk in the absence and in the presence of prognostic factors. If the value of the relative hazard ratio (HR) is greater than 1, the risk in the presence of prognostic factors is higher than that in the absence. If the prognostic factor is less than 1, the risk in the presence of prognostic factors is further reduced. The conversion of the relative hazard ratio to the log scale for each prognostic factor is called the coefficient for each factor and this value is used as the coefficient for calculating the BCT score model (Cox, David R. "Regression models and life-tables" J. Ournal of the Royal Statistical Society. Series B (Methodological) (1972): 187-220). The coefficient of the gene was verified the validity of the result of the equation through cross validation.

In the above equation, a value obtained by normalizing the expression level of each gene is substituted into each 'ΔCt_ prognosis prediction gene'. The normalization is accomplished through differences in expression amounts or expression levels of genes that may indicate differences in basal expression amounts or expression levels. Preferably, it calculates a ratio of an average expression amount of one to three genes (or the average of these expression amounts when a plurality of genes are selected) in CTBP1 (C-terminal-binding protein 1), CUL1 (cullin 1) and UBQLN1 (Ubiquilin-1).

Specifically, the value of "ΔCt-prognosis prediction gene" is a value obtained by adding 30 after the expression value of each prognostic gene was subtracted from the average expression value of the standard genes including CTBP1 (C-terminal-binding protein 1), CUL1 (cullin 1) and UBQLN1 (Ubiquilin-1) This value becomes a normalized value of each prognosis prediction gene. That is, the normalized value of each prognosis prediction gene is calculated by the following Equation:

(ΔCt_prognosis prediction gene=((Ct_CTBP1+Ct_CUL1+Ct_UBQLN1)/3)−Ct_prognosis prediction gene+30))

(The above-mentioned "prognosis prediction gene" refers to any one among UBE 2 C (Ubiquitin-conjugating enzyme E2C), TOP2A (Topoisomerase 2 alpha), RRM 2 (ribonucleotide reductase M2), FOXM 1 (Forkhead box M1), MKI 67 (Marker of proliferation Ki-67) and BTN3A2 (Butyrophilin subfamily 3 member A2).

The "Ct" refers to the number of cycles when a certain amount of PCR amplification product is amplified. In using the real-time RT-PCR method, since the change in the fluorescence intensity is generally equal to a noise level, which is equal to 0, when the number of amplification cycles is 1 to 10, such fluorescence intensity is regarded as a blank of the sample of the amplification product 0. A fluorescence value obtained by calculating the standard deviation SD thereof and multiplied by 10 is determined as a threshold value, and the number of PCR cycles first exceeding the threshold is regarded as a Ct (cycle threshold) value. Therefore, when the amplification product is large, the Ct value becomes a small value, and when the amplification product is small, the Ct value becomes a large value.

In the present invention, expression values of respective prognostic genes are normalized using standard genes, and the average Ct values of three standard genes are used to minimize technical errors that may occur in the test.

In the present invention, in order to express the calculated value of (Equation 1) as an intuitive numerical value, the calculated value is converted to a value between 0 and 10 by a linear transformation as shown in (Equation 2).

BCT score=0if 0.8*Unscaled BCT score(U-BS)−13.71<0

BCT score=0.8*U-BS−13.71

BCT score=10if 0.8*U-BS−13.71>10 (Equation 2) (BCT score calculation formula)

(f) predicting that the greater the numerical value calculated in the (e) is, the greater the effectiveness of chemotherapy is:

According to one example of the present invention, in the method of estimating the effectiveness of chemotherapy for the breast cancer patient according to the present invention, the point at which the sum of the sensitivity and the specificity as parameters for evaluating the accuracy of the risk group classification was maximized was calculated. As a result, we determined that when the numerical value calculated according to the above Equation 1 exceeded 22.1, the effectiveness of chemotherapy was high (high risk of metastasis), and when the value is 22.1 or less, the effectiveness of chemotherapy (low risk of metastasis) was low.

Meanwhile, in the case of Equation 2 (BCT score) obtained by linear transformation of Equation 1 (Unscaled BCT score), we determined that if the value is 4 or larger, the effectiveness of chemotherapy was high (metastatic high risk group) and if the value was less than 4, the effectiveness of chemotherapy is low (low risk of metastasis).

In the present invention, the "sensitivity" refers to the percentage of high-risk patients in the test results of patients who have metastasized within 10 years, and the 'specificity' refers to the percentage of low risk patients in the test results of patients who do not have metastasized for 10 years.

According to one embodiment of the present invention, the inventors analyzed using the Cox proportional hazards model to determine the statistical significance of the BCT score, and genes and clinical information used in the BCT score (i.e., cancer size and pN stage). As a result, the BCT score according to the present invention was confirmed to be more significant than the clinical information used as an index of general prognosis and the prognostic evaluation models such as NPI Score, PREDCIT and SNAP based on the clinical information.

According to another example of the present invention, the c-index of the BCT score and other models based on clinical information of the same patient group were compared. As a result, BCT score showed the highest c-index value, and it was confirmed that it showed higher prediction of breast cancer prognosis than other models.

Thus, the algorithm of the present invention can be used to screen patients who do not need additional chemotherapy after the primary breast cancer surgery. The subject group of the present algorithm of the present invention is preferably a group of patients who have not undergone any chemotherapy before and after surgery, and patients with a "good prognosis" have a low probability of metastasis, recurrence or metastatic recurrence within 10 years (low effectiveness of chemotherapy), but patients with 'poor prognosis' are more likely to develop metastasis, recurrence or metastatic recurrence within 10 years after surgery, and additional chemotherapy may be recommended (high effectiveness of chemotherapy) after surgery.

That is, the algorithm for predicting the effectiveness of chemotherapy of the breast cancer patient according to the above Equation 1 or Equation 1 and 2 of the present invention was obtained by analyzing proliferation-related genes, immune-related genes and clinical information (tumor size and pN stage) closely related to the prognosis of breast cancer from a wide range of clinical samples. The prediction of prognosis is greater than other models such as conventional prognostic evaluation model based on clinical information, and the prediction of the effectiveness of chemotherapy is also very accurate.

The present invention also provides a composition for predicting the effectiveness of chemotherapy in a breast cancer patient, the composition comprising agents for measuring the expression level of UBE2C, TOP2A, RRM2, FOXM1, MKI67 and BTN3A2 genes, respectively.

An embodiment according to another aspect of the present invention provides a composition for predicting the effectiveness of chemotherapy in a breast cancer patient, the composition consisting of agents for measuring the expression level of UBE2C, TOP2A, RRM2, FOXM1, MKI67 and BTN3A2 genes, respectively.

An embodiment according to still another aspect of the present invention provides a composition for predicting the effectiveness of chemotherapy in a breast cancer patient, the composition essentially consisting of agents for measuring the expression level of UBE2C, TOP2A, RRM2, FOXM1, MKI67 and BTN3A2 genes, respectively.

The present invention also provides a composition further comprises agents for measuring the expression level of CTBP1, CUL1 and UBQLN1 genes, respectively.

In the present invention, the agents for measuring the expression level of the genes may be a set of primer pair specifically binding to the UBE2C, TOP2A, RRM2, FOXM1, MKI67, BTN3A2, CTBP1, CUL1 and UBQLN1 genes.

As used herein, the term "primer" refers to an oligonucleotide which acts as a starting point for synthesis at conditions under which the synthesis of a primer extension product complementary to the nucleic acid chain (template) is induced, that is, a presence of polymerases such as a nucleotide and a DNA polymerase, and suitable temperature and pH. Preferably, the primer is a deoxyribonucleotide and a single strand. The primers used in the present invention may comprise naturally occurring dNMPs (i.e., dAMP, dGMP, dCMP and dTMP), modified nucleotides or non-natural nucleotides. The primers may also include ribonucleotides.

The primer of the present invention may be an extension primer that is annealed to a target nucleic acid and forms a sequence complementary to the target nucleic acid by a template-dependent nucleic acid polymerase. It extends to a position where the immobilization probe is annealed and occupies the area where it is annealed.

The extension primer used in the present invention comprises a hybridization nucleotide sequence complementary to the first position of the target nucleic acid. The term "complementary" means that the primer or probe is sufficiently complementary to hybridize selectively to the target nucleic acid sequence under certain annealing or hybridization conditions, and is substantially complementary and perfectly complementary, and preferably means completely complementary. As used herein, the term "substantially complementary sequence" used in relation to a primer sequence is meant to include not only a completely matched sequence but also a sequence partially inconsistent with the sequence to be compared within a range that can anneal to a specific sequence and serve as a primer.

The primer should be long enough to prime the synthesis of the extension product in the presence of polymerases. The suitable length of the primer is determined by a number of factors, such as the temperature, the application, and the source of the primer, but is typically 15-30 nucleotides. Short primer molecules generally require lower temperatures to form a sufficiently stable hybrid complex with the template. The term "annealing" or "priming" means that the oligodeoxynucleotide or hexane has apposition to the template nucleic acid, and the opposition allows the polymerase to polymerize the nucleotides to form complementary nucleic acid molecules in the template nucleic acid or a portion thereof.

The sequence of the primer does not need to have a sequence completely complementary to a partial sequence of the template, and it is sufficient if the primer has sufficient complementarity within a range that hybridizes with the template and can perform the primer-specific action. Therefore, the primer in the present invention does not need to have a perfectly complementary sequence to the nucleotide sequence as a template, and it is sufficient if the primer has sufficient complementarity within a range capable of hybridizing to the gene sequence and acting as a primer. The design of such a primer can be easily carried out by those skilled in the art with reference to the nucleotide sequence described above, for example, by using a program for primer design (e.g., PRIMER 3 program).

Preferably, the primer pair in the present invention is characterized by being composed of the sequence shown in SEQ ID NO: 1 to SEQ ID NO: 18. The primers and probe sequences of the selected genes for measuring the expression level of the genes in the present invention are shown in Table 3 below.

TABLE 3

Primer and probe sequence of gene for predicting prognosis of breast cancer

| Functional Classification | Gene | UPL probe | Forward primer | Reverse primer |
|---|---|---|---|---|
| Proliferation-related genes | UBE2C | SEQ ID NO: 19 GGGAAGGC | SEQ ID NO: 1 AAAAGGCTACAGCAG GAGC | SEQ ID NO: 2 AGCTGCTCCATGGAT GGTC |
| | TOP2A | SEQ ID NO: 20 GCCTCTGA | SEQ ID NO: 3 AAGAGTCATTCCACG AATAACCAT | SEQ ID NO: 4 GAGGGCTTCCTTCAG TATTT |
| | RRM2 | SEQ ID NO: 21 AAAGCCAG | SEQ ID NO: 5 TGGGAATCCCTGAAA CCC | SEQ ID NO: 6 GAACTTCTTGGCTAA ATCG |
| | FOXM1 | SEQ ID NO: 22 AGGCTGGA | SEQ ID NO: 7 AAGCACATTGCCAAG CCAGGC | SEQ ID NO: 8 CAGGGAAAGGTTGTG GCGG |
| | MKI67 | SEQ ID NO: 23 GAGGAGAG | SEQ ID NO: 9 CAGAATGAGAGCTCC CAGCCT | SEQ ID NO: 10 TGCATGAGAACCTTC GCACTC |
| Immune-related gene | BTN3A2 | SEQ ID NO: 24 CAAGGTGG | SEQ ID NO: 11 CTTCAAGCCTGGTGA GGA | SEQ ID NO: 12 TTTTCTGCAGTCTATT TTTCC |
| Standard genes | CTBP1 | SEQ ID NO: 25 GCCCCACG | SEQ ID NO: 13 CCTTGGGCATCATCGG A | SEQ ID NO: 14 GTTGAAGCCGAAGGC CTT |

TABLE 3-continued

Primer and probe sequence of gene for predicting prognosis of breast cancer

| Functional Classification | Gene | UPL probe | Forward primer | Reverse primer |
|---|---|---|---|---|
| | CUL1 | SEQ ID NO: 26 GCAGAGGC | SEQ ID NO: 15 AGTACTGAATTCTTGC AGCAGA | SEQ ID NO: 16 TCTTCGTTGTTCCTCA AGCAGAC |
| | UBQLN1 | SEQ ID NO: 27 TTGGGAGC | SEQ ID NO: 17 GAAATCCTCAGCTTCA GAACA | SEQ ID NO: 18 TGACATTGCTGATAGT GTATCA |

The present invention provides a kit for predicting the effectiveness of chemotherapy in a breast cancer patient, the kit comprising agents for measuring expression level of UBE2C, TOP2A, RRM2, FOXM1, MKI67 and BTN3A2 genes, respectively.

The present invention also provides a kit, wherein the kit further comprises agents for measuring expression level of the CTBP1, CUL1 and UBQLN1 genes, respectively.

The kit of the present invention may further comprise tools and/or reagents known in the art for use in RNA isolation and cDNA synthesis in PCR reaction reagents, in addition to a set of primer pair capable of amplifying the UBE2C, TOP2A, RRM2, FOXM1, MKI67, BTN3A2, CTBP1, CUL1 and UBQLN1 genes by PCR. The kit of the present invention may further comprise a tube, a well plate to be used for mixing the respective components and an instructional material describing the method of use, if necessary.

In addition, the present invention provides the use of agents for measuring expression level of UBE2C, TOP2A, RRM2, FOXM1, MKI67 and BTN3A2 genes for preparing agents for predicting the effectiveness of chemotherapy of breast cancer patient.

The present invention also provides the use of agents, wherein the agents for measuring the expression level further comprises agents for measuring the expression level of CTBP1, CUL1 and UBQLN1 genes, respectively.

The "agents for measuring expression level of the genes" of the present invention is the same as described above, the "genes for preparing agents for predicting the effectiveness of chemotherapy" is the same as described above, and is one or more selected from the group consisting of UBE2C, TOP2A, RRM2, FOXM1, MKI67, BTN3A2, CTBP1, CUL1, and UBQLN1.

The term "comprising" of the present invention is used synonymously with "containing" or "characterized" and does not exclude additional component elements or method steps not mentioned in the composition or method. The term "consisting of" means excluding additional elements, steps or components not otherwise mentioned. The term "essentially consisting of" refers to comprising a component element or step which is described in the range of a composition or a method and which does not substantially affect its basic.

Advantageous Effect

The present invention relates to a gene group showing a significant correlation with the prognosis of breast cancer, and a method for predicting the effectiveness of chemotherapy in a breast cancer patient using clinical information. Therefore, the method of the present invention can accurately predict the effectiveness of chemotherapy for the breast cancer patient, and can be used for the purpose of presenting clues about the direction of breast cancer treatment in the future.

MODE FOR CARRYING OUT INVENTION

Hereinafter, the present invention will be described in detail.

However, the following examples are illustrative of the present invention, and the present invention is not limited to the following examples.

Example 1

Collection of Expression Profiles of Early Breast Cancer Tissues

NCBI's Gene Expression Omnibus (GEO, www.ncbi.nlm.nih.gov/geo) is a database site where researchers gather large-scale experimental data on gene expression and mutations, such as a microarray. The data on this site can be reanalyzed freely, and the process of deriving this prognostic gene also used data from this site.

The microarray data used in this study were limited to data using a microarray chip called 'Affymetrix Human Genome U133A Array'.

There are about 22,000 probes on the chip, and each probe is a single gene. The degree of mRNA expression in most genes in the human body can be measured through the chip analysis.

In the NCBI GEO site, we examined microarray datasets for patients who were lymph node-negative patients and who were not treated with any chemotherapy after surgery. As a result, 684 specimen data from the following three datasets were obtained. The information on the sample dataset was shown in Tables 4 and 5 below.

TABLE 4

| GEO No. | GEO Registration year | Number of specimens | Specimen diagnosis (Date) | Retrospective observation period (Year) |
|---|---|---|---|---|
| GSE2034 | 2005 | 286 | 1980-1995 | 7.17 |
| GSE7390 | 2006 | 198 | 1980-1998 | 12.01 |
| GSE11121 | 2008 | 200 | 1988-1998 | 7.54 |

TABLE 5

Pathological information of clinical samples

| | Discovery data set | | |
|---|---|---|---|
| Characteristics | GSE2034 | GSE7390 | GSE11121 |
| Total | 286 (100%) | 198 (100%) | 200 (100%) |
| Age | | | |
| ≤40 | 36 (13%) | 42 (21.2%) | 10 (5%) |
| 41-55 | 129 (45%) | 129 (65.2%) | 64 (32%) |
| 56-70 | 89 (31%) | 27 (13.6%) | 83 (42%) |
| ≥70 | 32 (11%) | | 43 (22%) |
| Not available | | | |
| ER status | | | |
| ER+ | 209 (73.1%) | 134 (67.7%) | 156 (78%) |
| ER− | 77 (26.9%) | 64 (32.3%) | 44 (22%) |
| Not available | | | |
| Grade | | | |
| G1 | 7 (2%) | 30 (15.2%) | 29 (14.5%) |
| G2 | 42 (15%) | 83 (41.9%) | 136 (68.0%) |
| G3 | 148 (52%) | 83 (41.9%) | 35 (17.5%) |
| Not available | 89 (31%) | 2 (1.0%) | |
| T stage | | | |
| T1 | 146 (51%) | 107 (54%) | 112 (56.0%) |
| T2 | 132 (46%) | 91 (46.0%) | 85 (42.5%) |
| T3 | 8 (3%) | | 3 (1.5%) |
| Not available | | | |
| N stage | | | |
| N− | 286 (100%) | 198 (100%) | 200 (100%) |
| N+ | | | |
| Not available | | | |

Example 2

According to the distribution of Distant-Metastasis-free survival (DMFS), patients without distant metastatic recurrence for more than 10 years were classified as 'good prognosis group' and those with distant metastatic recurrence within 5 years were classified as 'bad prognosis group'. As a result of classifying the sample groups according to these classification criteria, it was classified that good prognosis group was 212 and bad prognosis group was 159. The mean DMFS was 13 years in the good prognosis group and 2.2 years in the poor prognosis group.

Example 3

Selection of Gene for Predicting Prognosis

We examined the genes whose expression levels differed between the prognostic groups through SAM (Significant Analysis of Microarray) analysis on 212 samples with good prognosis and 159 samples with poor prognosis. Using the q-values of the SAM analysis results, we selected overexpressed genes in a good prognosis group and overexpressed genes in a poor prognosis group. The selected genes are combined into one set. As a result, a total of 302 non-redundant sets of genes were created, and a clustering analysis was performed by Principal Component Analysis (PCA) to determine the expression pattern of these genes. Gene Ontology (GO) function analysis was performed for each cluster in order to select the two major components and to explore the related biological functions for each major component.

The results of GO analysis showed that the main component 1 was concentrated in the proliferation and the main component 2 was concentrated in the immune response. Genes were selected with the highest expression level between prognostic groups in the genes belonging to two major components involved in proliferation and immune response. For each gene set, the gene was named p-gene representing the expression pattern of proliferation and i-gene representing the expression pattern of the immune response. In the gene group classified as the p-gene or the i-gene, genes meeting the following conditions were selected as candidate genes for the gene prognosis diagnostic model:

(i) high relevance to immunity or immune response.

(ii) large difference in expression between specimens.

(iii) high expression value on average.

(iv) high correlation of expression between FFPE and frozen specimens in qRT-PCR results.

The gene groups selected according to the above criteria are as follows.

(1) 10 kinds of proliferation-related gene groups (p-genes): AURKA, CCNB2, FOXM1, MKI67, MMP11, PTTG1, RACGAP1, RRM2, TOP2A and UBE2C (2) Six kinds of immune response-related genes (i-genes): BTN3A2, CCL19, CD2, CD52, HLA. DPA1 and TRBC1

Example 4

Selection of Variables for Implementing Algorithm Predicting Breast Cancer Prognosis 4-1. Obtaining Samples for Algorithm Implementation We obtained 174 samples of a breast cancer patient who were not treated with chemotherapy at Samsung Hospital and Asan Hospital, used them to implement the algorithm, and used 227 samples for algorithm verification.

Clinical information of the obtained patient samples is shown in Table 6 below.

TABLE 6

Clinical information of clinical specimen of Samsung and Asan hospitals

| | Algorithm calculation test group | | Algorithm validation test group | |
|---|---|---|---|---|
| | No. of patients | % | No. of Patients | % |
| Samples | 174 | 100.00% | 227 | 100.00% |
| Age (years) | | | | |
| <50 | 66 | 37.93% | 109 | 48.02% |
| >=50 | 108 | 62.07% | 113 | 49.78% |
| NA | 0 | 0.00% | 5 | 2.20% |
| pN | | | | |
| 0 | 163 | 93.68% | 208 | 91.63% |
| 1 | 11 | 6.32% | 19 | 8.37% |
| Tumor size (cm) | | | | |
| ≤2 | 141 | 81.03% | 189 | 83.26% |
| 2-5 | 33 | 18.97% | 38 | 16.74% |
| >5 | 0 | 0.00% | 0 | 0.00% |
| Pathologic Stage | | | | |
| IA | 136 | 78.16% | 177 | 77.97% |
| IIA | 31 | 17.82% | 34 | 14.98% |
| IIB | 7 | 4.02% | 11 | 4.85% |
| NA | 0 | 0.00% | 5 | 2.20% |

TABLE 6-continued

Clinical information of clinical specimen
of Samsung and Asan hospitals

|  | Algorithm calculation test group | | Algorithm validation test group | |
|---|---|---|---|---|
|  | No. of patients | % | No. of Patients | % |
| Histologic Grade | | | | |
| 1 | 53 | 30.46% | 36 | 15.86% |
| 2 | 103 | 59.20% | 149 | 65.64% |
| 3 | 18 | 10.34% | 37 | 16.30% |

4-2. Selection of Genes to be Used for Prognosis Prediction

The RNAs of 16 genes previously selected were extracted from FFPE specimens and qRT-PCR was performed to calculate their expression values.

consistent with the direction of other studies and prognosis were selected as the genes to be used in the final algorithm.

The selected genes are five proliferation-related genes (UBE2C, TOP2A, MKI67, RRM2, and FOXM1) and one immune response-related gene (BTN3A2). Three additional standard genes (CTBP1, CUL1, and UBQLN1) suitable for FFPE tissue were selected from existing papers and their expression values were used for analysis ("Identification of novel reference genes using multiplatform expression data and their validation for quantitative gene expression analysis." PLoS One 4(7): e6162.2009).

4-3. Selection of Clinical Degree to Use in the Algorithm

Using the univariate Cox proportional hazards model, we identified the important clinical factors associated with metastatic recurrence in a breast cancer patient who were not treated with chemotherapy (p-value<0.05).

The results are shown in Table 7 below.

As shown in Table 7 below, pN, pathologic stage, tumor size and NPI score were found to be significant factors for distant metastasis.

TABLE 7

Significant clinical information for distant metastases through univariate Cox proportional hazards model

|  |  | All | | | Chemo | | | Non-chemo | | |
|---|---|---|---|---|---|---|---|---|---|---|
|  |  | HR | 95% CI | p-value | HR | 95% CI | p-value | HR | 95% CI | p-value |
| pN | 0 | 1.000 | | | 1.000 | | | 1.000 | | |
|  | 1 | 3.732 | 2.418  5.761 | 0.000 | 2.602 | 1.624  4.168 | 0.000 | 14.832 | 4.819  45.650 | 0.000 |
| pT | 1 | 1.000 | | | 1.000 | | | 1.000 | | |
|  | 2 | 1.888 | 1.217  2.928 | 0.005 | 1.302 | 0.806  2.102 | 0.281 | 4.668 | 1.568  13.900 | 0.006 |
|  | 3 | 1.999 | 0.617  6.471 | 0.248 | 1.360 | 0.416  4.441 | 0.611 | — | — — | — |
| Pathologic Stage | IA | 1.000 | | | 1.000 | | | 1.000 | | |
|  | IIA | 2.473 | 1.479  4.136 | 0.001 | 1.592 | 0.902  2.810 | 0.108 | 5.750 | 1.663  19.880 | 0.006 |
|  | IIB | 4.696 | 2.590  8.514 | 0.000 | 2.780 | 1.442  5.357 | 0.002 | 19.512 | 4.639  82.070 | 0.000 |
|  | IIIA | 5.934 | 1.399  25.170 | 0.016 | 3.738 | 0.868  16.091 | 0.077 | — | — — | — |
| Histologic Grade | 1 | 1.000 | | | 1.000 | | | 1.000 | | |
|  | 2 | 1.982 | 1.029  3.818 | 0.041 | 1.771 | 0.830  3.778 | 0.140 | 1.607 | 0.416  6.214 | 0.492 |
|  | 3 | 2.795 | 1.368  5.711 | 0.005 | 2.061 | 0.912  4.660 | 0.082 | 3.983 | 0.804  19.739 | 0.091 |
| Tumor Size | — | 1.271 | 1.121  1.441 | 0.000 | 1.131 | 0.969  1.321 | 0.119 | 4.579 | 2.275  9.217 | 0.000 |
| NPI | 1 | 1.000 | | | 1.000 | | | 1.000 | | |
|  | 2 | 2.894 | 1.679  4.986 | 0.000 | 1.828 | 0.996  3.355 | 0.051 | 7.652 | 2.240  26.140 | 0.001 |
|  | 3 | 4.257 | 2.415  7.507 | 0.000 | 2.650 | 1.436  4.893 | 0.002 | 12.233 | 2.236  66.930 | 0.004 |
|  | 4 | — | — — | — | — | — — | — | — | — — | — |
| NPI Score | — | 1.930 | 1.546  2.411 | 0.000 | 1.604 | 1.246  2.066 | 0.000 | 4.281 | 2.076  8.829 | 0.000 |
| Pathologic Stage | 1 | 1.000 | | | 1.000 | | | 1.000 | | |
|  | 2 | 2.963 | 1.837  4.777 | 0.000 | 1.868 | 1.099  3.174 | 0.021 | 7.809 | 2.552  23.900 | 0.000 |
|  | 3 | 5.920 | 1.396  25.112 | 0.016 | 3.729 | 0.866  16.057 | 0.077 | — | — — | — |
| Pathologic Stage | — | 2.802 | 1.836  4.275 | 0.000 | 1.8856 | 1.165  3.051 | 0.010 | 7.809 | 2.552  23.900 | 0.000 |
| Histologic Grade | — | 1.613 | 1.164  2.236 | 0.004 | 1.360 | 0.949  1.949 | 0.094 | 1.996 | 0.8522  4.673 | 0.111 |

Changes in the risk of distant metastasis due to increased expression of each gene can be verified using the Cox proportional hazards model. The hazard ratio (HR) is defined as the ratio of the risk of occurrence of an event (distant metastasis) according to presence or absence of a risk factor (gene) in a Cox proportional hazards model at a certain time interval. If this risk is greater than 1, the risk factor will increase the risk of the event, but if less than 1 means that the risk will decrease.

The proliferation-related genes classified as p-genes had a risk value of 1 or more, and if the larger the expression value was, the worse the prognosis was. However, the genes classified as i-genes had a risk value of less than 1 and it was confirmed that the larger the expression value was, the better the result of the prognosis was.

The importance of predicting prognosis among the observed genes is higher than other genes, and the genes Among these, tumor size was an important factor in distant metastatic recurrence in a breast cancer patient without chemotherapy, but not in a breast cancer patient who received chemotherapy.

The pN was significant in both patient groups without chemotherapy and with chemotherapy, but the hazard ratio values in patients without chemotherapy were seven times greater than those in chemically treated patients. In other words, the pN was found to be an index of more significant distant metastatic recurrence in patients who did not receive chemotherapy than patients who received chemotherapy.

The pathologic stage is also a significant factor but it is a concept that includes tumor size and pN. Because the NPI score is calculated based on the size of the cancer and the degree of lymph node metastasis, this index is also overlapped on the size of the cancer and the information on the pN. Finally, we selected tumor size and pN information for clinical information in a prognostic prediction model for patients who were not treated with chemotherapy.

Example 5

Derivation of the Equation of BCT Score Based on Cox Proportional Hazards Model 5-1. Derivation of the Equation The p-gene group (UBE2C, TOP2A, RRM2, FOXM1, and MKI67) of the proliferation-related genes shows a poor prognosis as the level of expression is increased, and the i-gene (BTN3A2) of the immune-related gene shows a good prognosis as the level of expression is increased. These genes were calculated by Cox proportional hazards analysis as follows.

(Equation of Unscaled BCT Score)

Unscaled BCT score(U-BS)=0.63*$\Delta Ct$_UBE2C+
0.32*$\Delta Ct$_TOP2A+0.13*$\Delta Ct$_RRM2+
0.02*$\Delta Ct$_FOXM1+0.04*$\Delta Ct$_MKI67−
0.42*$\Delta Ct$_BTN3A2+0.89*Tumor_size(cm)+
1.22*pN(0 or 1)

The Unscaled BCT score (U-BS) was calculated according to the above equation, and the distribution was confirmed. The results are shown in FIG. 1.

The cut-off of the BCT Score categorizes the patients as low risk or high risk for developing distant metastatic recurrence within 10 years. Evaluation variable of the accuracy of risk group classification is sensitivity and specificity. In the algorithm of the present invention, sensitivity and specificity are defined as follows.

Sensitivity: The percentage of high-risk patients who had a distant metastatic recurrence within 10 years.

Specificity: the percentage of low risk patients who did not have the distant metastatic recurrence within 10 years.

The larger the value of the sensitivity and specificity is, the better the classification is. However, increasing the sensitivity decreases the specificity, whereas increasing the specificity decreases the sensitivity. In the algorithm of the present invention, the BCT score classification point is calculated by calculating the cut-off point of the risk group classification so that the sum of the sensitivity and the specificity is maximized considering both the sensitivity and the specificity.

Figures 2A, 2B:
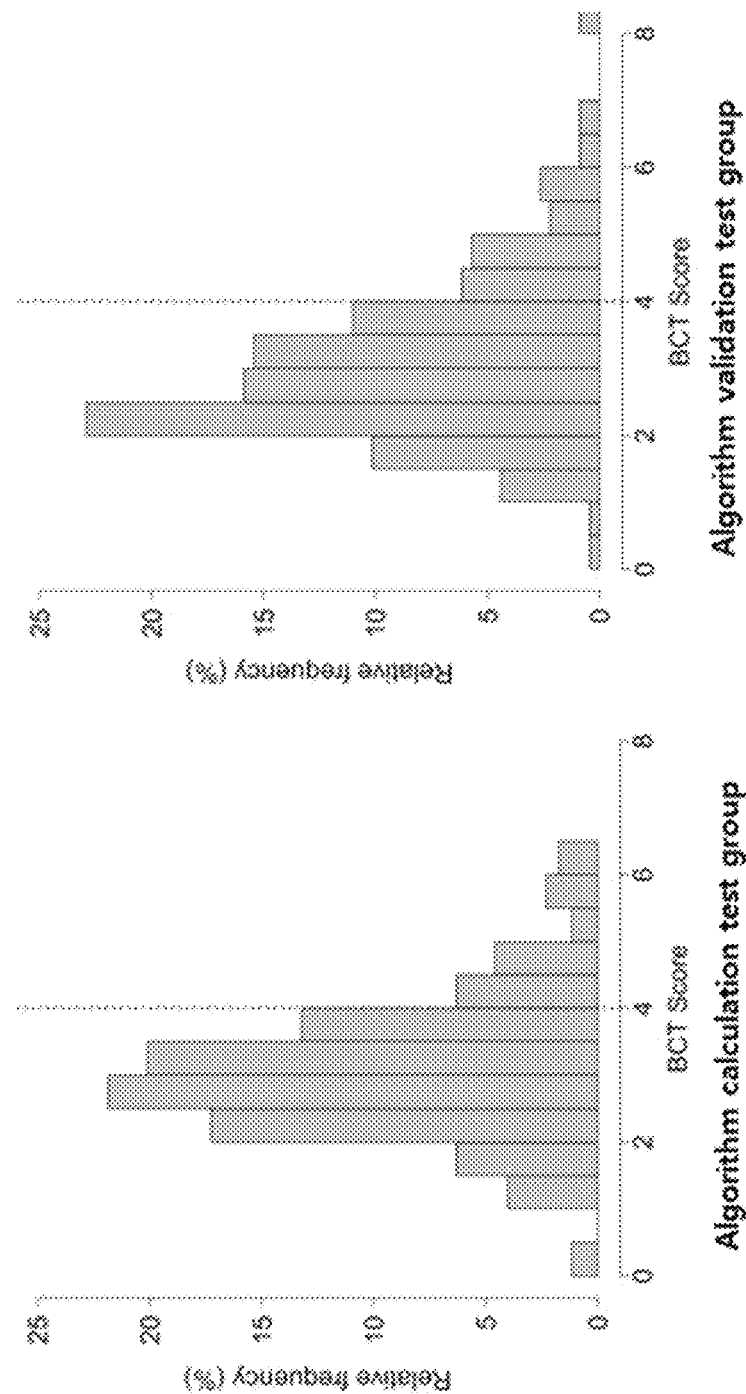
FIGS. 2A and 2B show the distribution of the BCT score in the algorithm calculation test group and the algorithm validation test group, respectively.

As shown in FIG. 2, the point at which the sum of the sensitivity and the specificity reaches a maximum according to the above criteria is 22.13767, which is designated as a threshold for distinguishing the high risk group from the low risk group. In other words, if the BCT score (BS) is 22.13767 or more, it can be classified as the high risk group of distant metastasis.

5-2. Derivation of Scaled Equation

In order to express the equation of Example 5-1 more intuitively, it was converted into a BCT score by linear transformation. The equation is as follows.

(The Equation of BCT Score (BS))

BCT score=0 if 0.8*U-BS−13.71<0

BCT score=0.8*U-BS−13.71

BCT score=10 if 0.8*U-BS−13.71>10

If the value of BCT score is less than 0, it is replaced with 0, and if it is larger than 10, it is converted into 10. As the BCT score increases, the possibility of cancer recurrence, metastasis or metastatic recurrence within 10 years is increased.

Figure 3B:
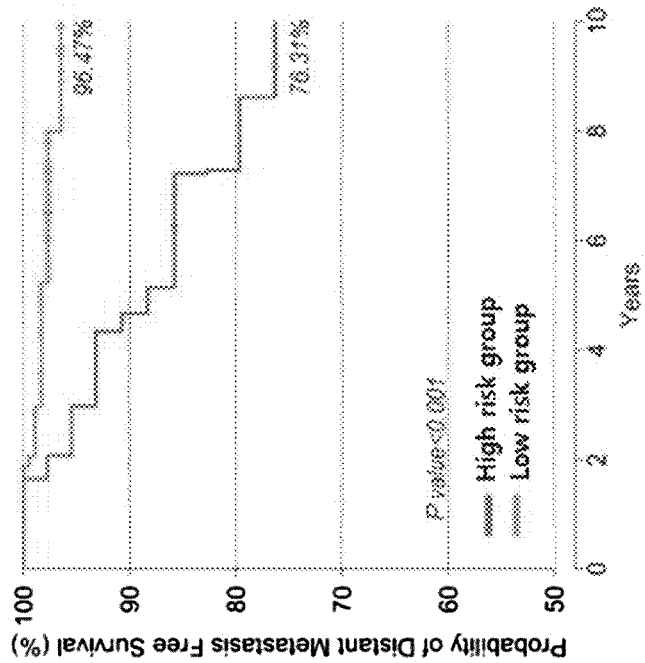
FIGS. 3A and 3B are graphs showing a distant metastasis-free survival in 10-year in the high risk group (a group having a high effectiveness of chemotherapy) and the low risk group (a group having a low effectiveness of chemotherapy) classified according to the BCT score in the algorithm calculation test group and the algorithm validation test group, respectively.
Figure 3A:
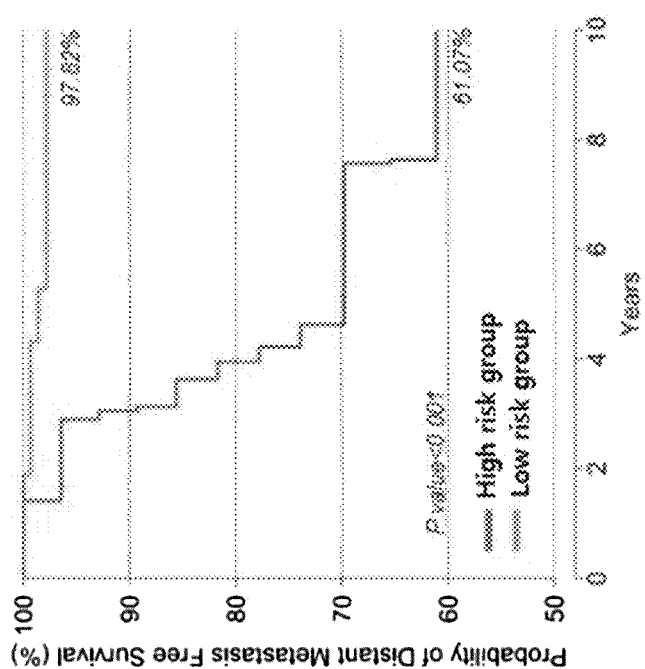

The BCT score was calculated according to the above equation and the distribution was confirmed. The results are shown in FIG. 2. As shown in FIG. 3, the threshold for classifying the patients in the high risk group and the low risk group for the distant metastasis was set to 4 (the point where the sum of the sensitivity and the specificity reached a maximum) in the BCT score. If the BCT score is 4 or more, it can be classified as high risk group with a recurrence, metastasis or metastatic recurrence and less than 4, it can be classified as low risk group.

Example 6

Performance Evaluation of Predicting Prognosis 6-1. Performance Evaluation Through Algorithm Calculation Test Group and Verification Test Group The high risk group classified according to the equation of Example 5 means that the recurrence, metastasis or metastatic recurrence may occur with a higher probability than the low risk group. FIG. 3 shows the results of estimation of distant metastasis recurrence probability through survival analysis of the algorithm calculation test group (discovery set) and the algorithm validation test group (validation set).

As shown in FIG. 3, the distant metastasis-free survival within 10 years in the low risk group based on the BCT score were 97.82% and 96.47% in the algorithm calculation test group and the algorithm validation test group, respectively. The distant metastasis-free survival within 10 years in the high risk group was 61.07% and 76.31%, respectively (p-values<0.001, log-rank test), indicating that there was a statistically significant difference in the distant metastasis free survival within 10 years in both test groups.

6-2. Statistical Significance Verification for Predicting Prognosis of BCT Score Using Univariate and Multivariate Cox Proportional Hazards Model To verify statistical significance for the prediction of distant metastasis of BCT score, we used the Cox proportional hazards analysis to determine whether it was more significant than clinical information and prognostic evaluation model based on clinical information.

As a result of the multivariate Cox proportional hazards analysis in the calculation test group and the verification test group of algorithm, the BCT score was confirmed to be a statistically significant index (p-values<0.05) in predicting distant metastasis compared with the general clinical information used as an index of prognosis.

Similarly, the BCT Score is a statistically significant indicator compared with the prognostic model based on clinical information and can be confirmed by multivariate Cox proportional hazards analysis (p-values<0.05).

TABLE 8

Multivariate Cox proportional hazards analysis of clinical information and prognostic prediction models

| | Algorithm calculation test group | | | Algorithm validation test group | | |
|---|---|---|---|---|---|---|
| | HR | 95% C.I. | P value | HR | 95% C.I. | P value |
| BCT Score | 2.22 | (1.08-4.58) | 0.030 | 1.88 | (1.10-3.21) | 0.022 |
| Age at surgery | 1.02 | (0.98-1.07) | 0.364 | 1.04 | (0.98-1.10) | 0.184 |
| Tumor Size | 1.50 | (0.47-4.74) | 0.494 | 0.79 | (0.33-1.89) | 0.597 |
| No. of LN metastasis | 1.53 | (0.77-3.04) | 0.220 | 0.17 | (0.02-1.42) | 0.103 |

TABLE 8-continued

Multivariate Cox proportional hazards analysis of clinical information and prognostic prediction models

| | Algorithm calculation test group | | | Algorithm validation test group | | |
|---|---|---|---|---|---|---|
| | HR | 95% C.I. | P value | HR | 95% C.I. | P value |
| Histologic Grade | 1.36 | (0.50-3.69) | 0.543 | 1.51 | (0.54-4.27) | 0.435 |
| BCT Score | 2.54 | (1.35-4.78) | 0.004 | 2.02 | (1.17-3.50) | 0.012 |
| NPI Score | 1.76 | (0.42-7.36) | 0.437 | 1.43 | (0.37-5.48) | 0.600 |
| PREDICT | 1.05 | (0.99-1.12) | 0.090 | 0.98 | (0.88-1.10) | 0.763 |
| SNAP | 0.93 | (0.74-1.18) | 0.545 | 0.91 | (0.71-1.16) | 0.438 |

6-3. Evaluation of Predictive Performance of Prognosis on of BCT Score Using C-Index The C-index has a value from 0.5 to 1. When the C-index is closer to the value of 0.5, the predictive possibility of prognosis is decreased, and when it is closer to 1, the predictive possibility of prognosis is increased. To evaluate the predictive possibility of prognosis of the BCT score, a clinical information-based model and a C-index comparative evaluation were performed.

Figures 4A, 4B:
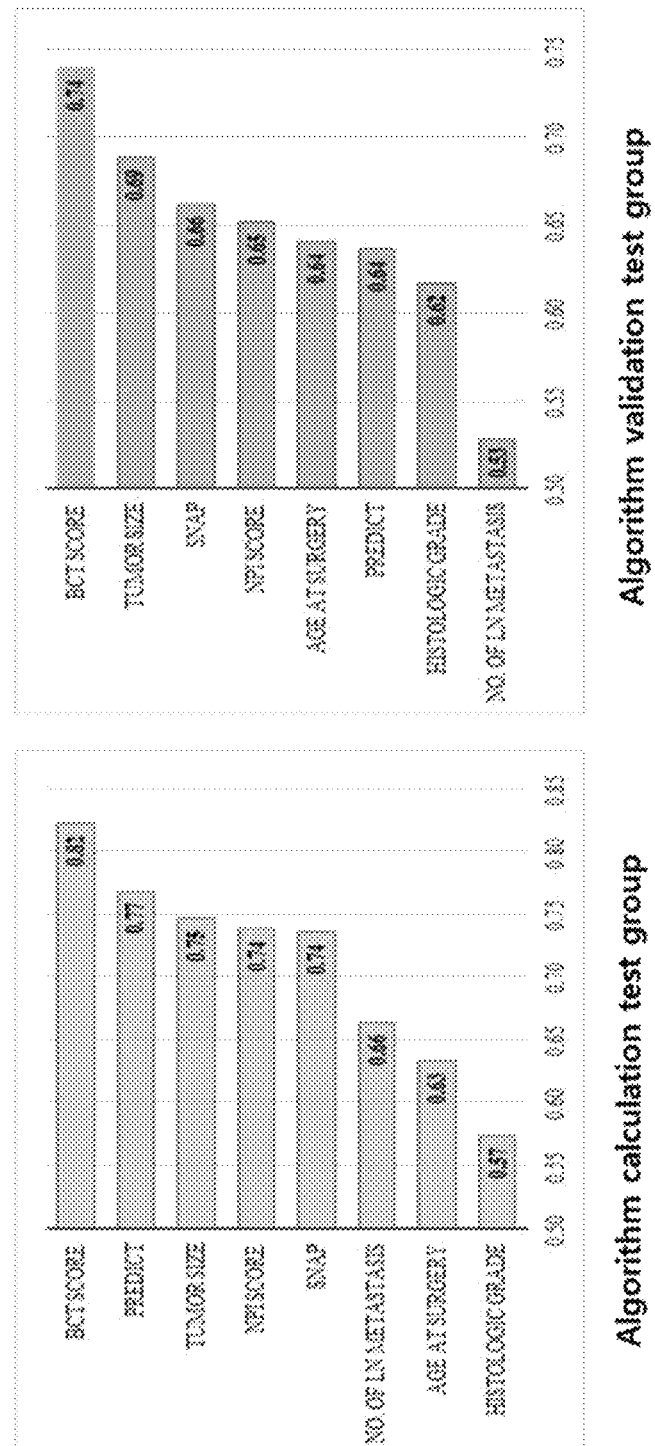
FIGS. 4A and 4B are graphs showing the results of the prediction performance evaluation of the prediction models of breast cancer prognosis through C-index in the algorithm calculation test group and the algorithm validation test group, respectively.

The c-index of the BCT score and other clinical information-based models were compared in the same patient group. As a result, BCT score showed the highest c-index value. This means that the BCT score had a higher predictive performance of prognosis than the other models of predicting prognosis (FIG. 4).

Example 7

Prediction of Effectiveness of Chemotherapy

The algorithm established in the above Examples 1 to 6 was used to confirm whether or not the effectiveness of chemotherapy in a breast cancer patient can be predicted.

The 346 patients who underwent surgery at Asan Hospital were used in this example. The specimens receiving chemotherapy and the specimens not receiving chemotherapy in the Example 4 were analyzed by the algorithm according to the present invention. They were classified into high risk and low risk groups, and the distant metastasis-free survival within 10 years according to patients treated with or without chemotherapy was compared.

Figures 5A, 5B:
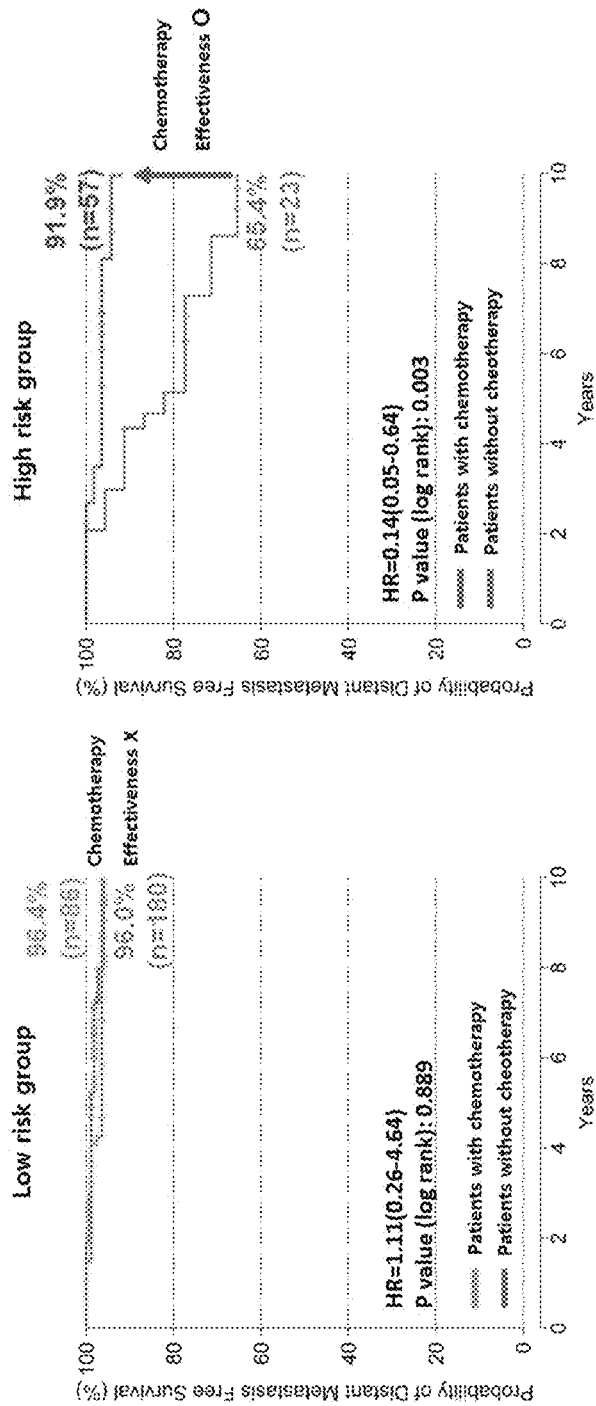
FIGS. 5A-5B are graphs showing the results of calculating the probability of distant metastasis-free survival for 10 years in patients who were treated with or without chemotherapy, after classifying the patients into low risk group (FIG. 5A) and high risk group (FIG. 5B) by an algorithm according to the present invention.
Figures 5C, 5D:
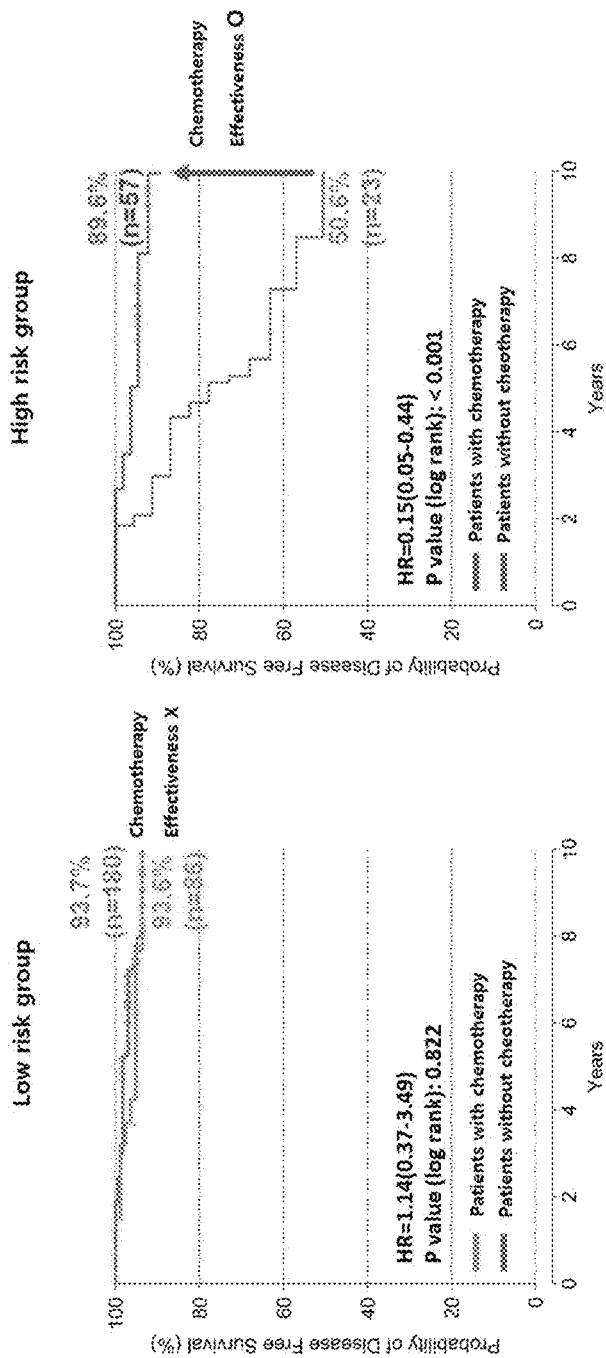
FIGS. 5C-5D are graphs showing the results of calculating the probability of disease free survival for 10 years in patients who were treated with or without chemotherapy, after classifying the patients into low risk group (FIG. 5C) and high risk group (FIG. 5D) by an algorithm according to the present invention.
Figures 5E, 5F:
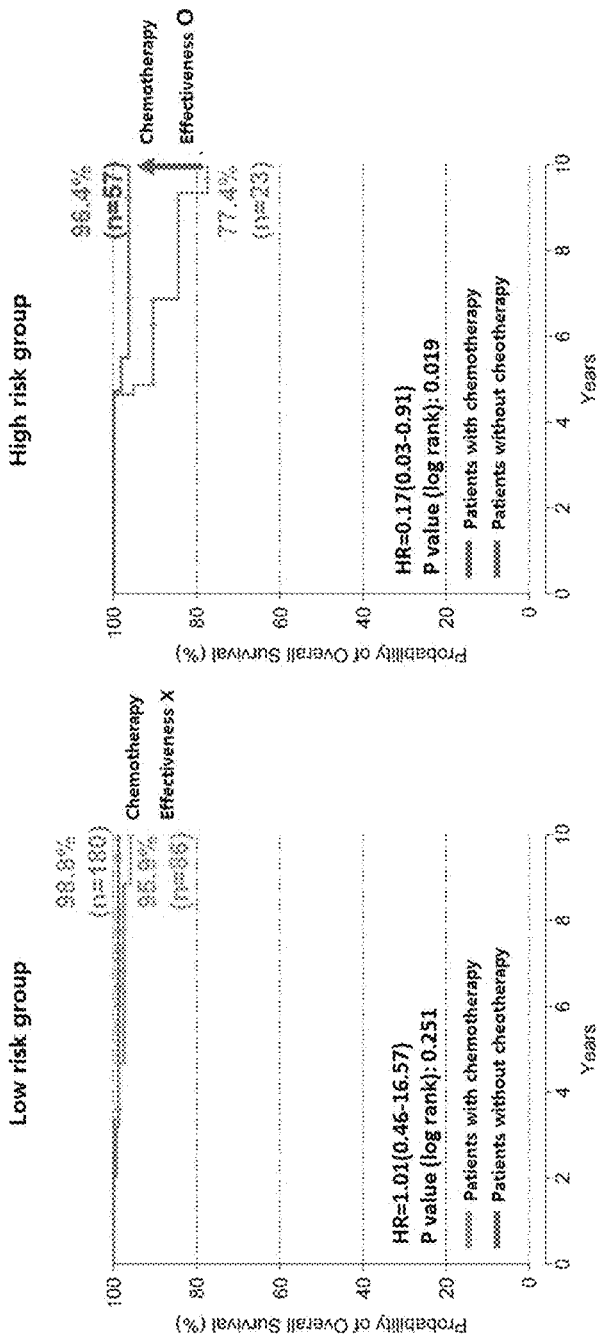
FIGS. 5E-5F are graphs showing the results of calculating the probability of overall survival for 10 years in patients who were treated with or without chemotherapy, after classifying the patients into low risk group (FIG. 5E) and high risk group (FIG. 5F) by an algorithm according to the present invention.

The specific clinical information of the patients was shown in Table 9, and the result of the probability of distant metastasis-free survival was shown in FIG. 5.

TABLE 9

| Total number of patients(346) | Number of patients | % |
|---|---|---|
| Age (Year) | | |
| <50 | 209 | 60.4% |
| ≥50 | 137 | 39.6% |
| Size of cancer (cm) | | |
| ≤2 | 231 | 66.8% |
| 2~5 | 113 | 32.7% |
| >5 | 2 | 0.6% |
| AJCC stage (7th ed.) | | |
| I | 231 | 66.8% |
| II | 115 | 33.2% |
| Histologic grade | | |
| 1 | 46 | 13.3% |
| 2 | 243 | 70.2% |
| 3 | 57 | 16.5% |
| NPI score | | |
| 1 | 204 | 59.0% |
| 2 | 118 | 34.1% |
| 3 | 24 | 6.9% |
| Secondary chemotherapy | | |
| Without chemotherapy | 203 | 58.7% |
| With chemotherapy | 143 | 41.3% |

As shown in FIG. 5, in the low risk group classified according to the algorithm of the present invention, the non-chemotherapy patient group had a probability of 96.0%, whereas the patients treated with chemotherapy had a probability of 96.4%. Thus, patients who received chemotherapy had a 0.4% increase in the distant metastasis-free survival. It can be concluded that there is no benefit of chemotherapy in low risk patients. On the other hand, in the high risk group classified according to the algorithm of the present invention, the distant metastasis-free survival of patients treated with chemotherapy had a probability 91.9%, whereas the non-chemotherapy patient group had a probability of 65.4%. Thus, we could confirm that it was statistically significant to be better in the prognosis of patients who received chemotherapy. Furthermore, according to the treatment or non-treatment with chemotherapy, it was confirmed that there was no significant difference in the survival probability in the low risk group but the effect of significant chemotherapy was showed in the high risk group in the disease-free survival probability and overall survival probability.

The results of univariate and multivariate analysis based on the Cox proportional hazards model for factors that could affect the distant metastasis-free survival in patients with each distinguished risk group according to the algorithm of the present invention were shown in Table 10. The chemotherapeutic treatment had no effect on the distant metastasis-free survival in low-risk group, and the treatment or non-treatment with chemotherapy in high risk group was found to be a factor affecting the distant metastasis-free survival of patients.

TABLE 10

| | Univariate analysis | | | Multivariate analysis | | |
|---|---|---|---|---|---|---|
| | HR | 95% C.I. | p-value | HR | 95% C.I. | p-value |
| High risk group (n = 80) | | | | | | |
| Age of Surgery | 1.08 | 1.01  1.15 | 0.020 | 1.05 | 0.07  0.97 | 0.138 |
| Cancer size (≤2 cm vs. >2 cm) | 0.55 | 0.16  1.88 | 0.342 | — | —  — | — |

TABLE 10-continued

|  | Univariate analysis | | | Multivariate analysis | | |
| --- | --- | --- | --- | --- | --- | --- |
|  | HR | 95% C.I. | p-value | HR | 95% C.I. | p-value |
| Histologic grade (Grade 1/2 vs. Grade 3) | 0.67 | 0.18  2.54 | 0.557 | — | — — | — |
| ER (IHC) | 1.14 | 0.76  1.71 | 0.514 | — | — — | — |
| PR (IHC) | 1.04 | 0.81  1.34 | 0.760 | — | — — | — |
| Chemotherapy (HTx vs. HTx + cTx) | 0.18 | 0.05  0.64 | 0.007 | 0.26 | 0.07  0.97 | 0.045 |
| Low risk group (n = 266) | | | | | | |
| Age of Surgery | 0.97 | 0.90  1.05 | 0.506 | — | — — | — |
| Cancer size (≤2 cm vs. >2 cm) | 0.52 | 0.06  4.23 | 0.542 | — | — — | — |
| Histologic grade (Grade 1/2 vs. Grade 3) | <0.01 | 0.00  Inf | 0.998 | — | — — | — |
| ER (IHC) | 0.99 | 0.60  1.62 | 0.969 | — | — — | — |
| PR (IHC) | 0.84 | 0.66  1.07 | 0.158 | — | — — | — |
| Chemotherapy (HTx vs. HTx + cTx) | 1.11 | 0.26  4.66 | 0.889 | — | — — | — |

Example 8

Predictability Comparison of Effectiveness of Chemotherapy

There is no benefit of chemotherapy in the low risk group of the present invention. It was confirmed more clearly when compared with a Modified Adjuvant! Online, a classification model of risk group based on clinical information. The Modified Adjuvant! Online predicts a degree of patient's risk based on the patient's clinical information and classifies the patients into high risk or low risk group. According to the algorithm of the present invention, we compared whether different distant metastasis-free survival of patients within 10 years was shown by Modified Adjuvant! Online, a model based on patient's clinical information among a total of 266 patients classified as low risk patients.

Figures 6A, 6B:
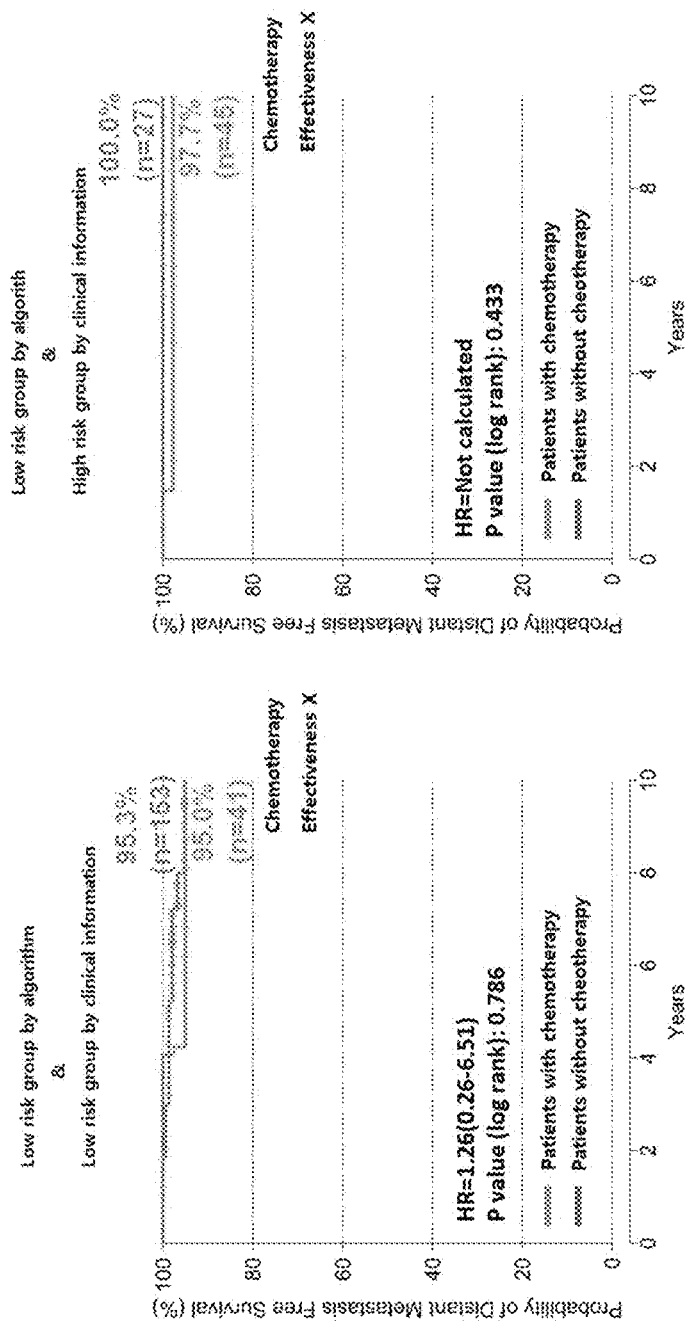
FIGS. 6A and 6B are graphs showing the results of confirming the difference of the probability of distant metastasis-free survival within 10 years in the patients classified as low risk based on the clinical information among the patients classified into the low risk group through an algorithm according to the present invention.

As shown in FIG. 6, the difference in the probability of distant metastasis-free survival of patients within 10 years according to the chemotherapy in patients classified as low risk group based on clinical information among the patients classified as low risk group by the algorithm according to the present invention was 0.3%. It was confirmed that patients without effectiveness of chemotherapy had no change of statistically significant distant metastasis-free survival by chemotherapy. Similarly, the difference in the distant metastasis-free survival of patients within 10 years in patients classified as high risk group based on clinical information among patients classified as low risk group by the algorithm according to the present invention was 2.3%. It was confirmed that there was no change in the statistically significant distant metastasis-free survival by chemotherapy.

Therefore, in the case of specific patients determined as a low risk group according to the algorithm of the present invention as patients diagnosed with breast cancer, it can be predicted that there will be no increase in the significant distant metastasis-free survival through chemotherapy. In the case of specific patients determined as a high risk group, it is predicted that the treatment of chemotherapy will have a better prognosis due to the high distant metastasis-free survival within 10 years after surgery.

INDUSTRIAL APPLICABILITY

The present invention relates to a gene group showing a significant correlation with the prognosis of breast cancer, and a method for predicting the effectiveness of chemotherapy in a breast cancer patient using clinical information. The method of the present invention can accurately predict the effectiveness of chemotherapy for the breast cancer patient. Therefore, it can be used for the purpose of presenting information on the direction of breast cancer treatment in the future, and is highly available in industry.

What is claimed is:

1. A method for treating a breast cancer in a breast cancer patient, the method comprising the steps of:
   (a) collecting a sample from the breast cancer patient;
   (b) determining in the sample the mRNA epression level values of a set of proliferation-related genes and an immune-related gene, wherein the proliferation-related genes comprise at least UBE2C (Ubiquitin-conjugating enzyme E2C), TOP2A (Topoisomerase 2 aplha), RRM2 (ribonucleotide reductase M2), FOXM1 (Fork-head box M1) and MKI67 (Marker of proliferation Ki-67), wherein the immune-related gene comprise at least BTN3A2 (Butyrophilin subfamily 3 member A2) and wherein the step of determining the mRNA expression level values comprises a step of using a plurality of primer pairs, wherein the plurality of the primer pairs comprises primer pairs for UBE2C, TOP2A, RRM2, FOXM1, MKI67, and BTN3A2 and wherein the primer pairs are selected to amplify the proliferation-related genes and the immune-related gene by PCR amplification;
(c) normalizing the mRNA expression level measured in the step (b);
(d) detecting in the sample an increase in normalized level of UBEC2, TOP2A, RRM2, FOXM1, and MKI67 or an increase in normalized value of BTN32; and
(e) treating the subject with an increased level of UBEC2, TOP2A, RRM2, FOXM1, and MKI67 with a treatment regimen comprising chemotherapy or treating the subject with an increase in BTN32 with a treatment regimen without chemotherapy.

2. The method of claim 1, wherein the breast cancer is a breast cancer which is an estrogen receptor-positive, a progesterone receptor-positive, or an estrogen receptor and progesterone receptor-positive, while being HER2-negative.

3. The method of claim 1, wherein the breast cancer is an early stage breast cancer classified as stage 1 or stage 2 according to the Tumor Node Metastasis (TNM) system.

4. The method of claim 1, wherein the step of normalizing comprises calculating a ratio of a mRNA expression level of each gene of UBE2C, TQP2A, RRM2, FQXM1, MKI67, and BTN3A2 to an average expression level of standard genes CTBP1 (C-terminal-binding protein 1), CUL1 (cullin 1) and UBQLN1 (Ubiquilin-1).

5. The method of claim 1, wherein the sample is selected from the group consisting of a formalin-fixed paraffin-embedded (FFPE) tissue, a fresh tissue, and a frozen tissue containing cancer cells of the patient.

6. The method of claim 1, wherein the expression level of the gene is measured by a method selected from the group consisting of RT-PCR, quantitative RT-PCR (qRT-PCR), real-time PCR.

* * * * *

SEQUENCE LISTING

<160> NUMBER OF SEQ ID NOS: 27

<210> SEQ ID NO 1
<211> LENGTH: 19
<212> TYPE: DNA
<213> ORGANISM: Artificial Sequence
<220> FEATURE:
<223> OTHER INFORMATION: UBE2C forward primer

<400> SEQUENCE: 1
aaaaggctac agcaggagc                                              19

<210> SEQ ID NO 2
<211> LENGTH: 19
<212> TYPE: DNA
<213> ORGANISM: Artificial Sequence

```
<220> FEATURE:
<223> OTHER INFORMATION: UBE2C reverse primer

<400> SEQUENCE: 2
agctgctcca tggatggtc                                                       19

<210> SEQ ID NO 3
<211> LENGTH: 24
<212> TYPE: DNA
<213> ORGANISM: Artificial Sequence
<220> FEATURE:
<223> OTHER INFORMATION: TOP2A forward primer

<400> SEQUENCE: 3
aagagtcatt ccacgaataa ccat                                                 24

<210> SEQ ID NO 4
<211> LENGTH: 20
<212> TYPE: DNA
<213> ORGANISM: Artificial Sequence
<220> FEATURE:
<223> OTHER INFORMATION: TOP2A reverse primer

<400> SEQUENCE: 4
gagggcttcc ttcagtattt                                                      20

<210> SEQ ID NO 5
<211> LENGTH: 18
<212> TYPE: DNA
<213> ORGANISM: Artificial Sequence
<220> FEATURE:
<223> OTHER INFORMATION: RRM2 forward primer

<400> SEQUENCE: 5
tgggaatccc tgaaaccc                                                        18

<210> SEQ ID NO 6
<211> LENGTH: 19
<212> TYPE: DNA
<213> ORGANISM: Artificial Sequence
<220> FEATURE:
<223> OTHER INFORMATION: RRM2 reverse primer

<400> SEQUENCE: 6
gaacttcttg gctaaatcg                                                       19

<210> SEQ ID NO 7
<211> LENGTH: 21
<212> TYPE: DNA
<213> ORGANISM: Artificial Sequence
<220> FEATURE:
<223> OTHER INFORMATION: FOXM1 forward primer

<400> SEQUENCE: 7
aagcacattg ccaagccagg c                                                    21

<210> SEQ ID NO 8
<211> LENGTH: 19
<212> TYPE: DNA
<213> ORGANISM: Artificial Sequence
<220> FEATURE:
<223> OTHER INFORMATION: FOXM1 reverse primer

<400> SEQUENCE: 8
cagggaaagg ttgtggcgg                                                       19
```

<210> SEQ ID NO 9
<211> LENGTH: 21
<212> TYPE: DNA
<213> ORGANISM: Artificial Sequence
<220> FEATURE:
<223> OTHER INFORMATION: MKI67 forward primer

<400> SEQUENCE: 9
cagaatgaga gctcccagcc t                                              21

<210> SEQ ID NO 10
<211> LENGTH: 21
<212> TYPE: DNA
<213> ORGANISM: Artificial Sequence
<220> FEATURE:
<223> OTHER INFORMATION: MKI67 reverse primer

<400> SEQUENCE: 10
tgcatgagaa ccttcgcact c                                              21

<210> SEQ ID NO 11
<211> LENGTH: 18
<212> TYPE: DNA
<213> ORGANISM: Artificial Sequence
<220> FEATURE:
<223> OTHER INFORMATION: BTN3A2 forward primer

<400> SEQUENCE: 11
cttcaagcct ggtgagga                                                  18

<210> SEQ ID NO 12
<211> LENGTH: 21
<212> TYPE: DNA
<213> ORGANISM: Artificial Sequence
<220> FEATURE:
<223> OTHER INFORMATION: BTN3A2 reverse primer

<400> SEQUENCE: 12
ttttctgcag tctatttttc c                                              21

<210> SEQ ID NO 13
<211> LENGTH: 17
<212> TYPE: DNA
<213> ORGANISM: Artificial Sequence
<220> FEATURE:
<223> OTHER INFORMATION: CTBP1 forward primer

<400> SEQUENCE: 13
ccttgggcat catcgga                                                   17

<210> SEQ ID NO 14
<211> LENGTH: 18
<212> TYPE: DNA
<213> ORGANISM: Artificial Sequence
<220> FEATURE:
<223> OTHER INFORMATION: CTBP1 reverse primer

<400> SEQUENCE: 14
gttgaagccg aaggcctt                                                  18

<210> SEQ ID NO 15
<211> LENGTH: 22
<212> TYPE: DNA
<213> ORGANISM: Artificial Sequence
<220> FEATURE:
<223> OTHER INFORMATION: CUL1 forward primer

```
<400> SEQUENCE: 15
agtactgaat tcttgcagca ga                                              22

<210> SEQ ID NO 16
<211> LENGTH: 23
<212> TYPE: DNA
<213> ORGANISM: Artificial Sequence
<220> FEATURE:
<223> OTHER INFORMATION: CUL1 reverse primer

<400> SEQUENCE: 16
tcttcgttgt tcctcaagca gac                                             23

<210> SEQ ID NO 17
<211> LENGTH: 22
<212> TYPE: DNA
<213> ORGANISM: Artificial Sequence
<220> FEATURE:
<223> OTHER INFORMATION: UBQLN1 forward primer

<400> SEQUENCE: 17
gaaatcctca gcttcaagaa ca                                              22

<210> SEQ ID NO 18
<211> LENGTH: 22
<212> TYPE: DNA
<213> ORGANISM: Artificial Sequence
<220> FEATURE:
<223> OTHER INFORMATION: UBQLN1 reverse primer

<400> SEQUENCE: 18
tgacattgct gatagtgtat ca                                              22

<210> SEQ ID NO 19
<211> LENGTH: 8
<212> TYPE: DNA
<213> ORGANISM: Artificial Sequence
<220> FEATURE:
<223> OTHER INFORMATION: UBE2C UPL probe

<400> SEQUENCE: 19 gggaaggc                                                               8

<210> SEQ ID NO 20
<211> LENGTH: 8
<212> TYPE: DNA
<213> ORGANISM: Artificial Sequence
<220> FEATURE:
<223> OTHER INFORMATION: TOP2A UPL probe

<400> SEQUENCE: 20 gcctctga                                                               8

<210> SEQ ID NO 21
<211> LENGTH: 8
<212> TYPE: DNA
<213> ORGANISM: Artificial Sequence
<220> FEATURE:
<223> OTHER INFORMATION: RRM2 UPL probe

<400> SEQUENCE: 21 aaagccag                                                               8

<210> SEQ ID NO 22
```

```
<211> LENGTH: 8
<212> TYPE: DNA
<213> ORGANISM: Artificial Sequence
<220> FEATURE:
<223> OTHER INFORMATION: FOXM1 UPL probe

<400> SEQUENCE: 22 aggctgga                                                                    8

<210> SEQ ID NO 23
<211> LENGTH: 8
<212> TYPE: DNA
<213> ORGANISM: Artificial Sequence
<220> FEATURE:
<223> OTHER INFORMATION: MKI67 UPL probe

<400> SEQUENCE: 23 gaggagag                                                                    8

<210> SEQ ID NO 24
<211> LENGTH: 8
<212> TYPE: DNA
<213> ORGANISM: Artificial Sequence
<220> FEATURE:
<223> OTHER INFORMATION: BTN3A2 UPL probe

<400> SEQUENCE: 24 caaggtgg                                                                    8

<210> SEQ ID NO 25
<211> LENGTH: 8
<212> TYPE: DNA
<213> ORGANISM: Artificial Sequence
<220> FEATURE:
<223> OTHER INFORMATION: CTBP1 UPL probe

<400> SEQUENCE: 25 gccccacg                                                                    8

<210> SEQ ID NO 26
<211> LENGTH: 8
<212> TYPE: DNA
<213> ORGANISM: Artificial Sequence
<220> FEATURE:
<223> OTHER INFORMATION: CUL1 UPL probe

<400> SEQUENCE: 26 gcagaggc                                                                    8

<210> SEQ ID NO 27
<211> LENGTH: 8
<212> TYPE: DNA
<213> ORGANISM: Artificial Sequence
<220> FEATURE:
<223> OTHER INFORMATION: UBQLN1 UPL probe

<400> SEQUENCE: 27 ttgggagc                                                                    8
```